United States Patent
Demont et al.

(10) Patent No.: US 8,846,709 B2
(45) Date of Patent: Sep. 30, 2014

(54) 7-(3,5-DIMETHYL-4-ISOXAZOLYL)-8-(METHYLOXY)-1H-IMIDAZO[4,5-C] QUINOLINE DERIVATIVES

(75) Inventors: Emmanuel Hubert Demont, Stevenage (GB); Katherine Louise Jones, Stevenage (GB); Robert J. Watson, Stevenage (GB)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 14/111,783

(22) PCT Filed: Apr. 19, 2012

(86) PCT No.: PCT/EP2012/057114
§ 371 (c)(1),
(2), (4) Date: Oct. 15, 2013

(87) PCT Pub. No.: WO2012/143416
PCT Pub. Date: Oct. 26, 2012

(65) Prior Publication Data
US 2014/0045834 A1     Feb. 13, 2014

(30) Foreign Application Priority Data

Apr. 21, 2011   (GB) ................................. 1106799.8

(51) Int. Cl.
*C07D 471/04*    (2006.01)
*A61K 31/437*    (2006.01)

(52) U.S. Cl.
CPC .................................. *C07D 471/04* (2013.01)
USPC .......................... 514/282; 546/82; 514/232.8

(58) Field of Classification Search
USPC .................................. 546/82; 514/282, 232.8
See application file for complete search history.

(56) References Cited

FOREIGN PATENT DOCUMENTS

WO      2004/058759 A1     7/2004
WO      2007/075468 A1     7/2007

*Primary Examiner* — Rita Desai
(74) *Attorney, Agent, or Firm* — Robert H. Brink

(57) ABSTRACT

Novel quinoline compounds pharmaceutical compositions containing such compounds and their use in therapy.

13 Claims, No Drawings

7-(3,5-DIMETHYL-4-ISOXAZOLYL)-8-(METHYLOXY)-1H-IMIDAZO[4,5-C]QUINOLINE DERIVATIVES

CROSS-REFERENCE TO RELATED APPLICATIONS

This application is filed pursuant to 35 USC 371 as a U.S. National Phase Application of International Patent Application Ser. No. PCT/EP2012/057114 filed on Apr. 19, 2012, which claims priority from 1106799.8 filed on Apr. 21, 2011 in the United Kingdom.

FIELD OF THE INVENTION

The present invention relates to novel compounds, pharmaceutical compositions containing such compounds and to their use in therapy.

BACKGROUND OF THE INVENTION

The genomes of eukaryotic organisms are highly organised within the nucleus of the cell. The long strands of duplex DNA are wrapped around an octomer of histone proteins (most usually comprising two copies of histones H2A, H2B H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRD-t) which contain tandem bromodomains capable of binding to two acetylated lysine residues in close proximity, increasing the specificity of the interaction. BRD2 and BRD3 are reported to associate with histones along actively transcribed genes and may be involved in facilitating transcriptional elongation (Leroy et al, Mol. Cell. 2008 30(1):51-60), while BRD4 appears to be involved in the recruitment of the pTEF-β complex to inducible genes, resulting in phosphorylation of RNA polymerase and increased transcriptional output (Hargreaves et al, Cell, 2009 138(1): 129-145). It has also been reported that BRD4 or BRD3 may fuse with NUT (nuclear protein in testis) forming novel fusion oncogenes, BRD4-NUT or BRD3-NUT, in a highly malignant form of epithelial neoplasia (French et al. Cancer Research, 2003, 63, 304-307 and French et al. Journal of Clinical Oncology, 2004, 22 (20), 4135-4139). Data suggests that BRD-NUT fusion proteins contribute to carcinogenesis (Oncogene, 2008, 27, 2237-2242). BRD-t is uniquely expressed in the testes and ovary. All family members have been reported to have some function in controlling or executing aspects of the cell cycle, and have been shown to remain in complex with chromosomes during cell division—suggesting a role in the maintenance of epigenetic memory. In addition some viruses make use of these proteins to tether their genomes to the host cell chromatin, as part of the process of viral replication (You et al Cell, 2004 117(3):349-60).

Japanese patent application JP2008-156311 discloses a benzimidazole derivative which is said to be a BRD2 bromodomain binding agent which has utility with respect to virus infection/proliferation.

Patent application WO2009084693A1 discloses a series of thienotriazolodiazepiene derivatives that are said to inhibit the binding between an acetylated histone and a bromodomain containing protein which are said to be useful as anti-cancer agents.

PCT patent application PCT/EP2010/066699 discloses a series of quinoline derivatives that inhibit the binding of BET family bromodomains with acetylated lysine residues.

A novel class of compounds have been found which inhibit the binding of bromodomains with its cognate acetylated proteins, more particularly a class of compounds that inhibit the binding of BET family bromodomains to acetylated lysine residues. Such compounds will hereafter be referred to as "bromodomain inhibitors".

SUMMARY OF THE INVENTION

In a first aspect of the present invention, there is provided a compound of formula (I) or a salt thereof, more particularly a compound of formula (I) or a pharmaceutically acceptable salt thereof

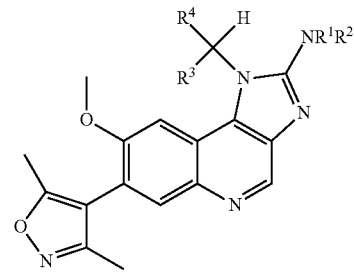

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

DETAILED DESCRIPTION OF THE INVENTION

The present invention relates to compounds of formula (I) or a salt thereof.

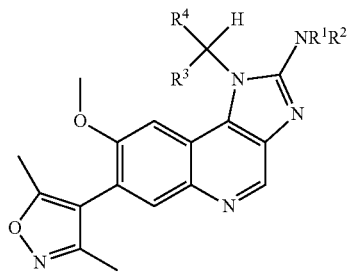

(I)

wherein:
$R^1$ is hydrogen or $C_{1-3}$alkyl and $R^2$ is selected from
hydrogen;
$C_{1-6}$alkyl; and
$C_{2-6}$alkyl substituted by hydroxy, $C_{1-4}$alkoxy or a group $NR^aR^b$ in which $R^a$ and $R^b$ are independently hydrogen or $C_{1-4}$alkyl, or $R^a$ and $R^b$ combine together with the N to which they are attached to form a heterocyclyl ring;
or
$R^1$ and $R^2$ combine together with the N to which they are attached to form a heterocyclyl ring;
$R^3$ is hydrogen, $C_{1-3}$alkyl or $CH_2OH$;
$R^4$ is selected from
a phenyl group optionally substituted by $C_{1-4}$alkyl, $CF_3$, halogen, hydroxy or $C_{1-4}$alkoxy;
a heteroaromatic group optionally substituted by $C_{1-4}$alkyl, $CF_3$, halogen, hydroxy or $C_{1-4}$alkoxy;
a tetrahydropyranyl group;
a tetrahydrofuranyl group;
a $C_{3-7}$cycloalkyl group; and
a $CH_2OMe$ group.

In one embodiment $R^1$ and $R^2$ combine together with the N to which they are attached to form a piperidinyl or morpholinyl ring.

In a further embodiment $R^1$ is hydrogen and $R^2$ is hydrogen or $C_{1-4}$alkyl (such as methyl, ethyl, isopropyl or isobutyl).

In a further embodiment $R^1$ is hydrogen and $R^2$ is $C_{2-4}$alkyl (such as methyl or ethyl) substituted by hydroxy or methoxy.

In a further embodiment $R^1$ is hydrogen and $R^2$ is $C_{2-4}$alkyl (such as ethyl) substituted by $NR^aR^b$ wherein $R^a$ and $R^b$ are both hydrogen or $R^a$ and $R^b$ combine together with the N to which they are attached form a morpholinyl ring.

In one embodiment $R^3$ is hydrogen and $R^4$ is tetrahydropyranyl.

In a further embodiment $R^3$ is hydrogen or methyl and $R^4$ is pyridyl (such as 2-pyridyl).

In a further embodiment $R^3$ is hydrogen or methyl and $R^4$ is pyrazolyl optionally substituted by $C_{1-4}$alkyl.

In a further embodiment $R^3$ is hydrogen or methyl and $R^4$ is phenyl.

In a further embodiment $R^3$ is methyl and $R^4$ is a group —$CH_2OMe$.

As used herein, the term "substituted" refers to substitution with the named substituent or substituents, multiple degrees of substitution being allowed unless otherwise stated. When the substituent is on a ring comprising a heteroatom the substituent may be located on a carbon or a heteroatom, if the latter is appropriate.

While the embodiments for each variable have generally been listed above separately for each variable, this invention is intended to include all combinations of embodiments described hereinabove including salts thereof.

Particular compounds according to the invention are:
2-({7-(3,5-dimethyl-4-isoxazolyl)-8-(methyloxy)-1-[(1R)-1-phenylethyl]-1H-imidazo[4,5-c]quinolin-2-yl}amino)ethanol;
2-{[7-(3,5-dimethyl-4-isoxazolyl)-8-(methyloxy)-1-(tetrahydro-2H-pyran-4-ylmethyl)-1H-imidazo[4,5-c]quinolin-2-yl]amino}ethanol;
7-(3,5-dimethyl-4-isoxazolyl)-8-(methyloxy)-1-(tetrahydro-2H-pyran-4-ylmethyl)-1H-imidazo[4,5-c]quinolin-2-amine;
7-(3,5-dimethyl-4-isoxazolyl)-8-(methyloxy)-1-(2-pyridinylmethyl)-1H-imidazo[4,5-c]quinolin-2-amine;
7-(3,5-dimethyl-4-isoxazolyl)-1-[1-methyl-2-(methyloxy)ethyl]-8-(methyloxy)-1H-imidazo[4,5-c]quinolin-2-amine;
7-(3,5-dimethyl-4-isoxazolyl)-N-ethyl-8-(methyloxy)-1-(tetrahydro-2H-pyran-4-ylmethyl)-1H-imidazo[4,5-c]quinolin-2-amine;
7-(3,5-dimethylisoxazol-4-yl)-N-ethyl-8-methoxy-1-(1-methoxypropan-2-yl)-1H-imidazo[4,5-c]quinolin-2-amine;
N1-(7-(3,5-dimethylisoxazol-4-yl)-8-methoxy-1-((tetrahydro-2H-pyran-4-yl)methyl)-1H-imidazo[4,5-c]quinolin-2-yl)ethane-1,2-diamine;
7-(3,5-dimethyl-4-isoxazolyl)-8-(methyloxy)-N-[2-(4-morpholinyl)ethyl]-1-(tetrahydro-2H-pyran-4-ylmethyl)-1H-imidazo[4,5-c]quinolin-2-amine;
7-(3,5-dimethyl-4-isoxazolyl)-8-(methyloxy)-N-[2-(methyloxy)ethyl]-1-(tetrahydro-2H-pyran-4-ylmethyl)-1H-imidazo[4,5-c]quinolin-2-amine;
7-(3,5-dimethyl-4-isoxazolyl)-N-ethyl-1-[1-methyl-2-(methyloxy)ethyl]-8-(methyloxy)-1H-imidazo[4,5-c]quinolin-2-amine;
N-[7-(3,5-dimethyl-4-isoxazolyl)-1-[1-methyl-2-(methyloxy)ethyl]-8-(methyloxy)-1H-imidazo[4,5-c]quinolin-2-yl]-1,2-ethanediamine;
7-(3,5-dimethyl-4-isoxazolyl)-1-[1-methyl-2-(methyloxy)ethyl]-8-(methyloxy)-N-[2-(4-morpholinyl)ethyl]-1H-imidazo[4,5-c]quinolin-2-amine;
7-(3,5-dimethyl-4-isoxazolyl)-1-[1-methyl-2-(methyloxy)ethyl]-8-(methyloxy)-N-[2-(methyloxy)ethyl]-1H-imidazo[4,5-c]quinolin-2-amine;
7-(3,5-dimethyl-4-isoxazolyl)-8-(methyloxy)-N-[2-(methyloxy)ethyl]-1-(2-pyridinylmethyl)-1H-imidazo[4,5-c]quinolin-2-amine;
7-(3,5-dimethyl-4-isoxazolyl)-8-(methyloxy)-2-(4-morpholinyl)-1-[(1R)-1-phenylethyl]-1H-imidazo[4,5-c]quinoline;
7-(3,5-dimethyl-4-isoxazolyl)-8-(methyloxy)-1-[(1R)-1-phenylethyl]-2-(1-piperidinyl)-1H-imidazo[4,5-c]quinoline;

7-(3,5-dimethyl-4-isoxazolyl)-8-(methyloxy)-2-(4-morpholinyl)-1-(tetrahydro-2H-pyran-4-ylmethyl)-1H-imidazo[4,5-c]quinoline;

7-(3,5-dimethylisoxazol-4-yl)-N-ethyl-8-methoxy-1-(1-(1-methyl-1H-pyrazol-4-yl)ethyl)-1H-imidazo[4,5-c]quinolin-2-amine;

7-(3,5-dimethylisoxazol-4-yl)-8-methoxy-N,N-dimethyl-1-((tetrahydro-2H-pyran-4-yl)methyl)-1H-imidazo[4,5-c]quinolin-2-amine; and 7-(3,5-dimethylisoxazol-4-yl)-8-methoxy-N-(2-methoxyethyl)-1-((R)-1-(pyridin-2-yl)ethyl)-1H-imidazo[4,5-c]quinolin-2-amine or a salt thereof.

Throughout the present specification, unless otherwise stated:

the term "halogen" is used to describe a group selected from fluorine, chlorine or bromine;

the terms "$C_{1-3}$alkyl", "$C_{1-4}$alkyl" and "$C_{1-6}$alkyl" are used to describe a group or a part of the group comprising a linear or branched alkyl group containing from 1 to 3, 1 to 4 or 1 to 6 carbon atoms respectively. Other references are to be similarly interpreted. Suitable examples of such groups include methyl, ethyl, propyl, isopropyl, n-butyl, isobutyl, t-butyl, pentyl and hexyl;

the term "$C_{1-4}$alkoxy" includes examples such as methyoxy, ethoxy, propyloxy isopropyloxy, n-butyloxy, isobutyloxy and t-butyloxy;

the term "$C_{3-7}$cycloalkyl" is used to describe a non-aromatic carbocyclic ring containing at least three and at most seven carbon atoms. Examples of $C_{3-7}$cycloalkyl include cyclopropyl, cyclobutyl, cyclopentyl, cyclohexyl and cycloheptyl.

As used herein, the term "heteroaromatic group" refers to a 5- or 6-membered monocyclic aromatic group wherein 1, 2, 3, 4 of the carbon atoms are replaced by a heteroatom independently selected from O, S and N; or to a 8- to 11-membered bicyclic aromatic group wherein 1, 2, 3, 4 or 5 of the carbon atoms are replaced by a heteroatom independently selected from O, S and N. Examples of 5- or 6-membered monocyclic heteroaromatic groups include pyrrolinyl, furanyl, thienyl, pyrrolyl, oxazolyl, thiazolyl, imidazolyl, oxadiazolyl, thiadiazolyl, pyridinyl, triazolyl, triazinyl, pyridazyl, pyrimidinyl, isothiazolyl, isoxazolyl, pyrazinyl, pyrazolyl and pyrimidinyl. Examples of 8- to 11-membered bicyclic heteroaromatic groups include 6H-thieno[2,3-b]pyrrolyl, imidazo[2,1-b][1,3]thiazolyl, imidazo[5,1-b][1,3]thiazolyl, indolyl, isoindolyl, indazolyl, benzimidazolyl, [1,3]thiazolo[3,2-b][1,2,4]triazolyl, benzoxazolyl e.g. benzoxazol-2-yl, benzisoxazolyl, benzothiazolyl, benzisothiazolyl, benzothienyl, benzofuranyl, naphthridinyl, quinolyl, quinoxalinyl, quinazolinyl, cinnolinyl and isoquinolyl.

As used herein the term "heterocyclyl" or "heterocyclyl ring" refers to a 4-7 membered non-aromatic, saturated ring comprising 1, 2, or 3 heteroatoms selected from O, N and S. Examples of such groups include pyrollidinyl, morpholinyl, piperidinyl and piperazinyl.

It will be appreciated that the present invention covers compounds of formula (I) as the free base and as salts thereof, for example as a pharmaceutically acceptable salt thereof. In one embodiment the invention relates to compounds of formula (I) or a pharmaceutically acceptable salt thereof.

Because of their potential use in medicine, salts of the compounds of formula (I) are desirably pharmaceutically acceptable. Suitable pharmaceutically acceptable salts can include acid or base addition salts. As used herein, the term 'pharmaceutically acceptable salt' means any pharmaceutically acceptable salt or solvate of a compound of formula (I), which upon administration to the recipient is capable of providing (directly or indirectly). In one embodiment, the term 'pharmaceutically acceptable salt' means any pharmaceutically acceptable salt of a compound of formula (I), which upon administration to the recipient is capable of providing (directly or indirectly). For a review on suitable salts see Berge et al., J. Pharm. Sci., 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable base addition salt can be formed by reaction of a compound of formula (I) with a suitable inorganic or organic base, (e.g. triethylamine, ethanolamine, triethanolamine, choline, arginine, lysine or histidine), optionally in a suitable solvent, to give the base addition salt which is usually isolated, for example, by crystallisation and filtration. Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

A pharmaceutically acceptable acid addition salt can be formed by reaction of a compound of formula (I) with a suitable inorganic or organic acid (such as hydrobromic, hydrochloric, sulphuric, nitric, phosphoric, succinc, maleic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

Other non-pharmaceutically acceptable salts, e.g. formates, oxalates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methylpyrrolidinone, methanol and ethanol may be used to form solvates. Methods for identification of solvates include, but are not limited to, NMR and microanalysis. Solvates of the compounds of formula (I) are within the scope of the invention.

The invention includes within its scope all possible stoichiometric and non-stoichiometric forms of the solvates of the compounds of formula (I).

The invention encompasses all prodrugs, of the compound of formula (I) or a pharmaceutically acceptable salt thereof, which upon administration to the recipient is capable of providing (directly or indirectly) the compound of formula (I) or a pharmaceutically acceptable salt thereof, or an active metabolite or residue thereof. Such derivatives are recognizable to those skilled in the art, without undue experimentation. Nevertheless, reference is made to the teaching of Burger's Medicinal Chemistry and Drug Discovery, $5^{th}$ Edition, Vol 1: Principles and Practice, which is incorporated herein by reference to the extent of teaching such derivatives.

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

Certain compounds described herein may contain one or more chiral atoms so that optical isomers, e.g. enantiomers or diastereoisomers may be formed. Accordingly, the present invention encompasses all isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography or HPLC.

Certain compounds of formula (I) may exist in one of several tautomeric forms. It will be understood that the present invention encompasses all tautomers of the compounds of formula (I) whether as individual tautomers or as mixtures thereof.

It will be appreciated from the foregoing that included within the scope of the invention are solvates, isomers and polymorphic forms of the compounds of formula (I) and salts thereof.

The compounds of formula (I) or salts thereof may be made by a variety of methods, including standard chemistry. Any previously defined variable will continue to have the previously defined meaning unless otherwise indicated. Illustrative general synthetic methods are set out below and then specific compounds of formula (I) and pharmaceutically acceptable salts thereof, are prepared in the working Examples. These processes form further aspects of the present invention.

In a further aspect there is provided a process for the preparation of a compound of formula (I) which comprises a process selected from (a), (b), (c), (d) and (e) in which (a) comprises reacting a compound of formula (II)

(II)

in which $R^3$ and $R^4$ are as defined in formula (I) and Hal is halogen with a compound of formula (III)

$NR^1R^2$ (III)

in which $R^1$ and $R^2$ are as defined in formula (I).

(b) comprises reacting a compound of formula (IV)

(IV)

in which $R^3$ and $R^4$ are as defined in formula (I) with a compound of formula $S=C=NR^1R^2$ (V)

in which $R^1$ and $R^2$ are as defined in formula (I);

(c) when $NR^1R^2$ is $NH_2$, reacting a compound of formula (IV) with cynanogen bromide;

(d) comprises reacting a compound of formula (IV) as defined above with a compound of formula (VI)

(VI)

(e) comprises reacting a compound of formula (IV) as defined above with a compound of formula (VII)

(VII)

Process (a)

A suitable Hal group is chloro. The reaction between the compound of formula (II) and formula (III) may be carried out in an inert solvent optionally in the presence of a base.

Compounds of formula (II) can be prepared by methods described herein or by analogous methods thereto. Compounds of formula (III) are commercially available.

Process (b)

The reaction between the compound of formula (IV) and formula (V) may be carried out in an inert solvent (such as methanol). Compounds of formula (IV) can be prepared by methods described herein or by analogous methods thereto. Compounds of formula (V) are commercially available.

Process (c)

The reaction between the compound of formula (IV) and formula (V) may be carried out in an inert solvent (such as ethanol). Compounds of formula (IV) can be prepared by methods described herein or by analogous methods thereto. Cynanogen bromide is commercially available.

Process (d)

The reaction between the compound of formula (IV) and formula (VI) may be carried out in an inert solvent (such as acetonitrile). Compounds of formula (IV) can be prepared by methods described herein or by analogous methods thereto. Compounds of formula (VI) are commercially available.

Process (e)

The reaction between the compound of formula (IV) and formula (VII) may be carried out in an inert solvent (such as ethanol). Compounds of formula (VII) can be prepared by methods described in Eur. J. Org. Chem. 2010 (19) 3641-3649.

It will be appreciated by those skilled in the art that it may be advantageous to protect one or more functional groups of the compounds described above. Examples of protecting groups and the means for their removal can be found in T. W. Greene 'Protective Groups in Organic Synthesis' (4th edition, J. Wiley and Sons, 2006). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—COCF$_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above are believed to be novel and therefore form a yet further aspect of the invention.

The compounds of formula (I) and salts thereof are bromodomain inhibitors, and thus are believed to have potential utility in the treatment of diseases or conditions for which a bromodomain inhibitor is indicated.

The present invention thus provides a compound of formula (I) or a pharmaceutically acceptable salt thereof for use in therapy. The compound of formula (I) or a pharmaceutically salt thereof can be used in the treatment of diseases or conditions for which a bromodomain inhibitor is indicated.

The present invention thus provides a compound of formula (I) or a pharmaceutically acceptable salt thereof for use in the treatment of any diseases or conditions for which a bromodomain inhibitor is indicated. In another embodiment there is provided a compound or a pharmaceutically acceptable salt thereof for use in the treatment of chronic autoimmune and/or inflammatory conditions. In a further embodiment there is provided a compound or a pharmaceutically acceptable salt thereof for use in the treatment of cancer.

Also provided is the use of a compound of formula (I) or a pharmaceutically acceptable salt thereof in the manufacture of a medicament for the treatment of diseases or conditions for which a bromodomain inhibitor is indicated.

Also provided is a method of treating diseases or conditions for which a bromodomain inhibitor is indicated in a subject in need thereof which comprises administering a therapeutically effective amount of compound of formula (I) or a pharmaceutically acceptable salt thereof.

Suitably the subject in need thereof is a mammal, particularly a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, atherosclerosis, Alzheimer's disease, depression, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (kerartoconjunctivitis Sicca), vernal keratoconjunctivitis, atopic keratoconjunctivitis, anterior uveitis, pan uveitis, posterior uveits, uveitis-associated macula edema. scleritis, diabetic retinopathy, diabetic macula edema, age-related macula dystrophy, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement and acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid scar formation, scleroderma (including morphea) and cardiac fibrosis.

Bromodomain inhibitors may be useful in the prevention and treatment of viral infections such as herpes virus, human papilloma virus, adenovirus and poxvirus and other DNA viruses.

Bromodomain inhibitors may be useful in the treatment of cancer, including hematological (such as leukaemia, lymphoma and multiple myeloma), epithelial (including lung, breast and colon carcinomas), midline carcinomas, mesenchymal, hepatic, renal and neurological tumours.

Bromodomain inhibitors may be useful in the treatment of dermal pathology such as non-malignant melanoma (actinic keratosis and basal cell), in-situ melanoma, squamous cell carcinoma and cutaneous T-cell lymphoma.

In one embodiment the disease or condition for which a bromodomain inhibitor is indicated is selected from diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac and gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

In one embodiment the disease or condition for which a bromodomain inhibitor is indicated is selected from herpes simplex infections and reactivations, cold sores, herpes zoster infections and reactivations, chickenpox, shingles, human papilloma virus, human immunodeficiency virus (HIV), cervical neoplasia, adenovirus infections, including acute respiratory disease, poxvirus infections such as cowpox and smallpox and African swine fever virus. In one particular embodiment a bromodomain inhibitor is indicated for the treatment of Human papilloma virus infections of skin or cervical epithelia.

The term "diseases or conditions for which a bromodomain inhibitor is indicated", is intended to include each of or all of the above disease states.

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more pharmaceutically acceptable carriers, diluents or excipients. The compounds of formula (I) and pharmaceutically acceptable salts, are as described above. The carrier(s), diluent(s) or excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable carriers, diluents or excipients. The pharmaceutical composition can be used in the treatment of any of the conditions described herein.

Since the compounds of formula (I) are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral or sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

A preferred dosage form that results in occlusion and modification of skin permeation either to increase or decrease the systemic exposure of bromodomain compounds, including but not limited to the pharmaceutically acceptable forms of carboxymethylcellulose, an aliginate, gelatine or polyvinyl pyrrolidone.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof, can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical solution, suspension, emulsion, ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

An ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl)acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) Adv. Drug Deliv. Rev. 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metals salts of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354.

A therapeutically effective amount of a compound of formula (I) or a pharmaceutically acceptable salt thereof, will depend upon a number of factors including, for example, the age and weight of the animal, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.5 to 1000 mg, of a compound of formula (I) or a pharmaceutically acceptable salt thereof, calculated as the free base. Each dosage unit for nasal or inhaled administration preferably contains from 0.001 to 50 mg, more preferably 0.01 to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example, an oral or parenteral dose of 0.01 mg to 3000 mg per day or 0.5 to 1000 mg per day, or a nasal or inhaled dose of 0.001 to 50 mg per day or 0.01 to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof, and may be employed alone or in combination with other therapeutic agents. Combination therapies according to the present invention thus comprise the administration of at least one compound of formula (I) or a pharmaceutically acceptable salt thereof, and the use of at least one other pharmaceutically active agent. Preferably, combination therapies according to the present invention comprise the administration of at least one compound of formula (I) or a pharmaceutically acceptable salt thereof, and at least one other pharmaceutically active agent. The compound(s) of formula (I) and pharmaceutically acceptable salts thereof, and the other pharmaceutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other pharmaceutically active agent(s) and the relative timings of administration will be selected in order to achieve the desired combined therapeutic effect. Thus in a further aspect, there is provided a combination comprising a compound of formula (I) or a pharmaceutically acceptable salt thereof, and at least one other pharmaceutically active agent.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists beta-2 agonists and Vitamin D3 analogues. In a further aspect a compound of formula (I) or a pharmaceutically acceptable salt thereof, according to the invention may be used in combination with a further therapeutic agent which is suitable for the treatment of cancer.

It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The compounds of formula (I) and pharmaceutically acceptable salts thereof, may be prepared by the methods described below or by similar methods. Thus the following Intermediates and Examples serve to illustrate the preparation of the compounds of formula (I) and pharmaceutically acceptable salts thereof, and are not to be considered as limiting the scope of the invention in any way.

General Experimental Details

All temperatures referred to are in ° C.

The names of the following compounds have been obtained using the compound naming programme "ACD Name Pro 6.02" or Chem Draw Ultra 12.0.

Abbreviations

| | |
|---|---|
| NMP | N-Methyl-2-pyrrolidone |
| AcOH | acetic acid |
| DCM | dichloromethane |
| DME | 1,2-dimethoxyethane |
| DMF | N,N-dimethylformamide |
| HOBT | 1-(hydroxy)benzotriazole |
| EDC | 1-ethyl-3-(3-dimethylaminopropyl)carbodiimide |
| diethyl ether | diethyl ether |
| EtOAc | ethyl acetate |
| i-Pr$_2$O | di-isopropyl ether |

-continued

| | |
|---|---|
| CH$_3$CN | acetonitrile |
| MeOH | methanol |
| THF | tetrahydrofuran |
| RT | room temperature |
| Rt | retention time |
| DIPEA | N,N-diisopropylethylamine |
| CS$_2$ | carbon disulfide |
| Na$_2$CO$_3$ | sodium carbonate |
| NaHCO$_3$ | sodium hydrogen carbonate |
| NaNO$_2$ | sodium nitrite |
| NaOH | sodium hydroxide |
| Na$_2$SO$_4$ | sodium sulfate |
| POCl$_3$ | Phosphorus (III) oxychloride |
| Pd/C | Palladium on carbon |
| mCPBA | m-chloroperbenzoic acid |
| CDCl$_3$ | deuterated chloroform |
| MTBE | Methyl t-butylether |
| BOC | tert-butyloxycarbonyl |
| PEPPSI catalyst | [1,3-Bis(2,6-Diisopropylphenyl)imidazol-2-ylidene](3-chloropyridyl)palladium(II) dichloride |
| DMSO-d6 | deuterated dimethylsulfoxide |
| N | 1 Normal (concentration) |

LC/MS Methodology
Method Formate (Formic Acid Modifier)
LC Conditions

The UPLC analysis was conducted on an Acquity UPLC BEH C18 column (50 mm×2.1 mm, i.d. 1.7 μm packing diameter) at 40° C.

The solvents employed were:
A=0.1% v/v solution of formic acid in water
B=0.1% v/v solution of formic acid in acetonitrile The gradient employed was:

| Time (min) | Flow rate (ml/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 0 | 100 |

The UV detection was a summed signal from wavelength of 210 nm to 350 nm.

MS Conditions
MS: Waters ZQ
Ionisation mode: Alternate-scan positive and negative electrospray
Scan range: 100 to 1000 AMU
Scan time: 0.27 sec
Inter scan delay: 0.10 sec
Method HpH (Ammonium Bicarbonate Modifier)
LC Conditions The UPLC analysis was conducted on an Acquity UPLC BEH C18 column (50 mm×2.1 mm, i.d. 1.7 μm packing diameter) at 40° C.

The solvents employed were:
A=10 mM ammonium hydrogen carbonate in water adjusted to pH10 with ammonia solution
B=acetonitrile The gradient employed was:

| Time (min) | Flow rate (ml/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 0 | 100 |

The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.27 sec
Inter scan delay: 0.10 sec
MDAP Methodology
Method Formate
LC Conditions The HPLC analysis was conducted on either a Sunfire C18 column (100 mm×19 mm, i.d 5 μm packing diameter) or a Sunfire C18 column (150 mm×30 mm, i.d. 5 μm packing diameter) at ambient temperature.

The solvents employed were:
A=0.1% v/v solution of formic acid in water
B=0.1% v/v solution of formic acid in acetonitrile
Run as a gradient over either 15 or 25 min (extended run) with a flow rate of 20 ml/min (100 mm×19 mm, i.d 5 μm packing diameter) or 40 ml/min (150 mm×30 mm, i.d. 5 μm packing diameter).

The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.50 sec
Inter scan delay: 0.20 sec
Method HpH
LC Conditions The HPLC analysis was conducted on either an Xbridge C18 column (100 mm×19 mm, i.d 5 μm packing diameter) or a Xbridge C18 column (100 mm×30 mm, i.d. 5 μm packing diameter) at ambient temperature.

The solvents employed were:
A=10 mM ammonium bicarbonate in water, adjusted to pH10 with ammonia solution
B=acetonitrile
Run as a gradient over either 15 or 25 min (extended run) with a flow rate of 20 ml/min (100 mm×19 mm, i.d 5 μm packing diameter) or 40 ml/min (100 mm×30 mm, i.d 5 μm packing diameter).

The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.50 sec
Inter scan delay: 0.20 sec In the procedures that follow, after each starting material, reference to an Intermediate by number is typically provided. This is provided merely for assistance to the skilled chemist. The starting material may not necessarily have been prepared from the batch referred to.

Where reference is made to the use of a "similar" procedure or "similarly prepared", as will be appreciated by those skilled in the art, such a procedure may involve minor variation, for example reaction temperature, reagent/solvent amount, reaction time, work-up conditions or chromatographic purification conditions.

Intermediate 1

3,5-dimethyl-4-[2-(methyloxy)-5-nitrophenyl]isoxazole

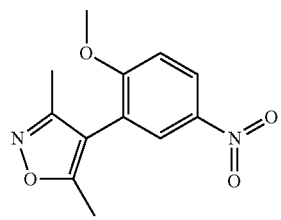 [SMILES: COc1ccc([N+](=O)[O-])cc1-c1c(C)noc1C]

3-Iodo-4-(methoxy)nitrobenzene (50 g, 179 mmol), (3,5-dimethyl-4-isoxazolyl)boronic acid (27.8 g, 197 mmol) and cesium carbonate (117 g, 358 mmol) were combined in a 500 ml RBF with DME (80 ml) and water (40 ml) and the mixture was degassed with nitrogen for 10 min, then PEPPSI catalyst (3.04 g, 4.48 mmol) was added and the mixture was heated at 90° C. for 4 h under a nitrogen atmosphere. The cooled reaction was diluted with EtOAc (800 ml), the organic layer was separated and washed with 10% sodium sulphite solution. The solvent was dried and evaporated in vacuo to give a brown solid which was triturated with ether (200 ml) and the solid product washed with ether (100 ml) to give 3,5-dimethyl-4-[2-(methyloxy)-5-nitrophenyl]isoxazole (43.9 g, 177 mmol, 99% yield) as a beige solid LCMS (formate) Rt 0.99 min, MH+ 249

Intermediate 2

[3-(3,5-dimethyl-4-isoxazolyl)-4-(methyloxy)phenyl]amine

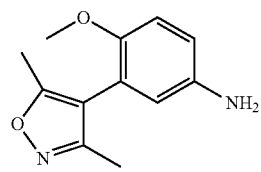 [SMILES: COc1ccc(N)cc1-c1c(C)noc1C]

3,5-Dimethyl-4-[2-(methyloxy)-5-nitrophenyl]isoxazole (for a preparation see Intermediate 1) (43.9 g, 177 mmol) was dissolved in EtOAc (1 liter) diluted with ethanol (1 liter) and added to Pd/C (8 g, 5% w/w, 50% water, Type E101 NO/W) in a 5 liter hydrogenation flask under vacuum, having first purged the vessel twice with vacuum/nitrogen cycles. The mixture was stirred for 24 h. No hydrogen uptake for the first 8-10 h, then steady uptake till approximately 20 liters had been consumed. The mixture purged with vacuum/nitrogen cycle×3 then was filtered through Celite™ under nitrogen and the filtrate evaporated in vacuo to give [3-(3,5-dimethyl-4-isoxazolyl)-4-(methyloxy)phenyl]amine 3-(3,5-dimethyl-4- isoxazolyl)-4-(methyloxy)aniline (38.6 g, 177 mmol, 100% yield) as a brown crystalline solid. LCMS (formate) Rt 0.50 min, MH+ 219

Intermediate 3

Diethyl({[3-(3,5-dimethyl-4-isoxazolyl)-4-(methyloxy)phenyl]amino}methylidene)propanedioate

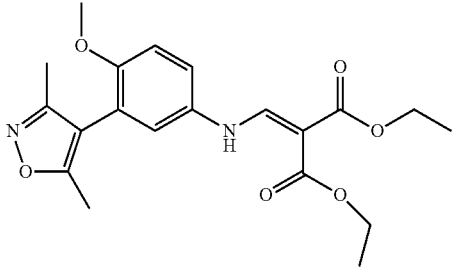 [SMILES: CCOC(=O)C(=CNc1ccc(OC)c(-c2c(C)noc2C)c1)C(=O)OCC]

[3-(3,5-Dimethyl-4-isoxazolyl)-4-(methyloxy)phenyl] amine (for a preparation see Intermediate 2) (39 g, 179 mmol) was dissolved in diethyl [(ethyloxy)methylidene]propanedioate (38.6 g, 179 mmol) and heated to 130° C., giving a steady effervescence as ethanol boiled off. The solution was heated for 1 h, then cooled to room temperature and evaporated in vacuo to give a brown oil. The product was dissolved in DCM (100 ml) and loaded onto a 750 g silica column, then eluted with 0-100% EtOAc/cyclohexane to give diethyl({[3-(3,5-dimethyl-4-isoxazolyl)-4-(methyloxy)phenyl] amino}methylidene)propanedioate (59.5 g, 153 mmol, 86% yield) as pale yellow crystalline solid. LCMS (formate) Rt 1.15 min, MH+ 389.

Intermediate 4

Ethyl 7-(3,5-dimethyl-4-isoxazolyl)-4-hydroxy-6-(methyloxy)-3-quinolinecarboxylate

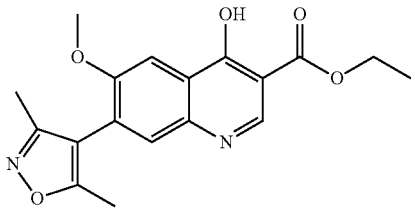 [SMILES: CCOC(=O)c1cnc2cc(-c3c(C)noc3C)c(OC)cc2c1O]

Diethyl({[3-(3,5-dimethyl-4-isoxazolyl)-4-(methyloxy) phenyl]amino}methylidene)propanedioate (for a preparation see Intermediate 3) (35 g, 90 mmol) was added in small portions over 10 min to boiling diphenyl ether (500 ml)—vigorous effervescence results. The mixture was heated at reflux for 20 min, the heater was switched off and removed from the vessel and the solution allowed to cool in air over 2 h to 40° C., giving some precipitation of a brown granular solid. The mixture was diluted with ether (300 ml) and allowed to stand overnight, then filtered and the solid washed with ether (2×200 ml) and dried to give ethyl 7-(3,5-dimethyl-4-isoxazolyl)-4-hydroxy-6-(methyloxy)-3-quinolinecarboxylate (28.4 g, 83 mmol, 92% yield). LCMS (formate) Rt 0.73 min, MH+ 343

Intermediate 5

7-(3,5-dimethyl-4-isoxazolyl)-4-hydroxy-6-(methyloxy)-3-quinolinecarboxylic acid

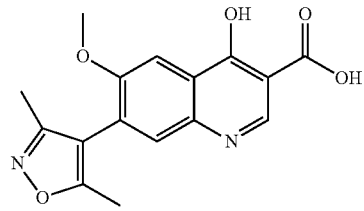 [SMILES: COc1cc2c(O)c(C(=O)O)cnc2cc1-c1c(C)noc1C]

Ethyl 7-(3,5-dimethyl-4-isoxazolyl)-4-hydroxy-6-(methyloxy)-3-quinolinecarboxylate (for a preparation see Intermediate 4) (28.4 g, 83 mmol) was suspended in a mixture of ethanol (200 ml) and NaOH (2M, 124 ml, 249 mmol) and the mixture was heated at reflux overnight, then evaporated to around 100 ml volume and the resulting solution washed with MTBE (100 ml). The aqueous layer was acidified to pH4 with 1M HCl, then the resulting solid collected by filtration and washed with water and dried overnight at 40° C. in the vacuum oven to give 7-(3,5-dimethyl-4-isoxazolyl)-4-hydroxy-6-(methyloxy)-3-quinolinecarboxylic acid (24.5 g, 78 mmol, 94% yield) as pale yellow solid. LCMS Rt 0.76 min, MH+ 315

Intermediate 6

7-(3,5-dimethyl-4-isoxazolyl)-6-(methyloxy)-4(1H)-quinolinone

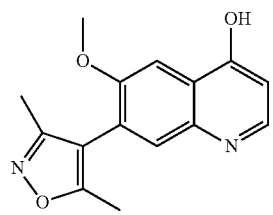 [SMILES: COc1cc2c(O)ccnc2cc1-c1c(C)noc1C]

7-(3,5-Dimethyl-4-isoxazolyl)-6-(methyloxy)-4-oxo-1,4-dihydro-3-quinolinecarboxylic acid (for a preparation see Intermediate 5) (8 g, 25.5 mmol) was added in small portions to refluxing diphenyl ether (150 ml) and the resulting solution was stirred for 30 min, then allowed to cool to 35° C. before addition of diethyl ether (200 ml). The resulting suspension was filtered and the solid product washed with ether (100 ml) to give 7-(3,5-dimethyl-4-isoxazolyl)-6-(methyloxy)-4(1H)-quinolinone (6.9 g, 25.5 mmol, 100% yield) as a beige solid. LCMS (formate) Rt 0.61, MH+ 271.

Intermediate 7

7-(3,5-dimethyl-4-isoxazolyl)-6-(methyloxy)-3-nitro-4-quinolinol

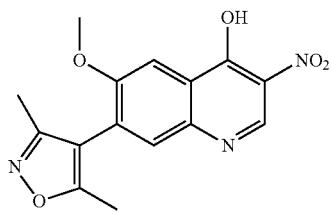 [SMILES: COc1cc2c(O)c([N+](=O)[O-])cnc2cc1-c1c(C)noc1C]

Nitric acid (1.86 g, 1.32 ml, 29.5 mmol) was added dropwise to a stirred solution of 7-(3,5-dimethyl-4-isoxazolyl)-6-(methyloxy)-4(1H)-quinolinone (for a preparation see Intermediate 6) (6.9 g, 25.6 mmol) in propionic acid (70 ml). After complete addition the reaction mixture was stirred at 100° C. for 1 h. The reaction mixture was cooled to room temperature, the solid was filtered off, washed with diethyl ether and dried to give 7-(3,5-dimethyl-4-isoxazolyl)-6-(methyloxy)-3-nitro-4-quinolinol (5.0 g, 15.86 mmol, 62.1% yield) as a bright yellow solid. LCMS (formate) Rt 1.15 min, MH+ 316

Intermediate 8

4-(4-chloro-6-methoxy-3-nitroquinolin-7-yl)-3,5-dimethylisoxazole

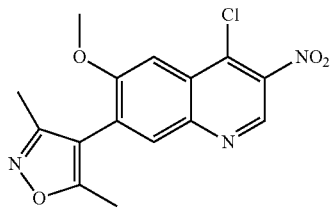 [SMILES: COc1cc2c(Cl)c([N+](=O)[O-])cnc2cc1-c1c(C)noc1C]

7-(3,5-Dimethylisoxazol-4-yl)-6-methoxy-3-nitroquinolin-4(1H)-one (for a preparation see Intermediate 6) (4.78 g, 15.16 mmol) was dissolved in POCl₃ (10 ml, 107 mmol) and the mixture was heated at 110° C. for 3 h, then cooled and evaporated in vacuo, The residue was suspended in toluene (20 ml) and evaporated in vacuo, then the residue was suspended in DCM (100 ml) and saturated sodium hydrogen carbonate solution (100 ml) and stirred for 10 min. The organic layer was dried and evaporated and the residue dissolved in DCM (10 ml) and loaded onto a 100 g silica column, then eluted with 0-60% EtOAc/cyclohexane to give 4-(4-chloro-6-methoxy-3-nitroquinolin-7-yl)-3,5-dimethylisoxazole (3.21 g, 9.62 mmol, 63.4% yield) as a bright yellow powder. LCMS (formate) Rt 1.13 min, MH+ 334

Intermediate 9

4-chloro-7-(3,5-dimethyl-4-isoxazolyl)-6-(methyloxy)-3-quinolinecarboxamide

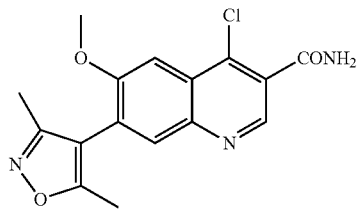 [SMILES: COc1cc2c(Cl)c(C(N)=O)cnc2cc1-c1c(C)noc1C]

7-(3,5-Dimethyl-4-isoxazolyl)-6-(methyloxy)-4-oxo-1,4-dihydro-3-quinolinecarboxylic acid (for a preparation see Intermediate 5) (36 g, 115 mmol) was heated in POCl₃ (33 ml, 354 mmol) for 4 h, then allowed to cool to room temperature and stood overnight. The mixture was evaporated on a rotary evaporator, then the brown residue was azeotroped to dryness with toluene (2×300 ml) and the resulting dark brown gum dissolved in THF (300 ml) and added dropwise to concentrated ammonium hydroxide solution (100 ml, 0.880), cooling in an ice bath. The mixture was stirred for 30 min, then evaporated to half volume, diluted with water (100 ml) and the resulting dark brown solid collected by filtration, washed with water (100 ml) and dried in vacuum oven at 50° C. for three days to give 4-chloro-7-(3,5-dimethyl-4-isoxazolyl)-6-(methyloxy)-3-quinolinecarboxamide (33.2 g, 100 mmol, 87% yield) as brown solid. LCMS (formate) Rt 0.80 min, MH+ 332

Intermediate 10

7-(3,5-dimethyl-4-isoxazolyl)-6-(methyloxy)-4-{[(1R)-1-phenylethyl]amino}-3-quinolinecarboxamide 4-Chloro-7-(3,5-dimethyl-4-isoxazolyl)-6-(methyloxy)-3-quinolinecarboxamide (for a preparation see Intermediate 9) (3.33 g, 10.04 mmol) was dissolved in NMP (10 ml) and DIPEA (1.8 ml, 10 mmol) and [(1R)-1-phenylethyl]amine (1.58 g, 13.05 mmol) were added, then the solution was heated at 120° C. for 18 h, then cooled to room temperature, diluted with water (100 ml) and extracted with EtOAc (2×100 ml). The organic layer was washed with water (2×100 ml), dried with sodium sulphate and evaporated in vacuo to give a brown gum. This was dissolved in DCM 20 ml) and loaded onto a 100 g silica cartridge, then eluted with MeOH/DCM (0-10%) and product-containing fractions evaporated in vacuo to give 7-(3,5-dimethyl-4-isoxazolyl)-6-(methyloxy)-4-{[(1R)-1-phenylethyl]amino}-3-quinolinecarboxamide (3.5 g, 8.40 mmol, 84% yield) as a beige solid. LCMS (formate) Rt 0.84 min, MH+ 417

Intermediate 11

7-(3,5-dimethyl-4-isoxazolyl)-8-(methyloxy)-1-[(1R)-1-phenylethyl]-1,3-dihydro-2H-imidazo[4,5-c]quinolin-2-one

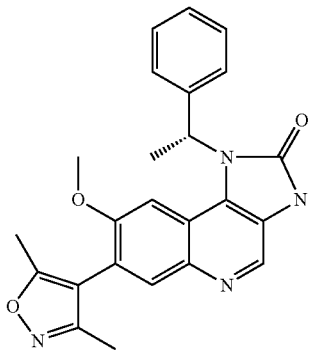 [SMILES: COc1cc2c(cc1-c1c(C)noc1C)ncc1[nH]c(=O)n([C@H](C)c3ccccc3)c12]

7-(3,5-Dimethyl-4-isoxazolyl)-6-(methyloxy)-4-{[(1R)-1-phenylethyl]amino}-3-quinolinecarboxamide (for a preparation see Intermediate 10) (3.3 g, 7.92 mmol) was dissolved in methanol (50 ml) and cooled in an ice bath, then potassium hydroxide (0.667 g, 11.89 mmol) was added and the solution stirred for 20 min, then iodobenzene diacetate (3.32 g, 10.30 mmol) was added and the mixture was stirred for a further 3 h. The solution was evaporated in vacuo and the residue was dissolved in DCM and loaded onto a 100 g silica column, then eluted with MeOH/DCM (0-10%) to give 7-(3,5-dimethyl-4-isoxazolyl)-8-(methyloxy)-1-[(1R)-1-phenylethyl]-1,3-dihydro-2H-imidazo[4,5-c]quinolin-2-one (2.03 g, 4.90 mmol, 61.8% yield) as beige foam. LCMS (formate) Rt 0.99 min, MH+ 415

Intermediate 12

2-chloro-7-(3,5-dimethyl-4-isoxazolyl)-8-(methyloxy)-1-[(1R)-1-phenylethyl]-1H-imidazo[4,5-c]quinoline

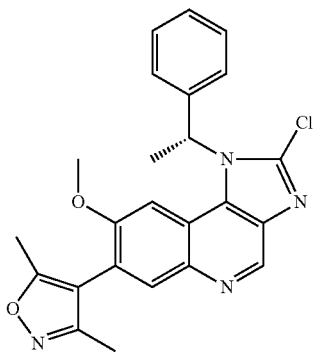 [SMILES: COc1cc2c(cc1-c1c(C)noc1C)ncc1nc(Cl)n([C@H](C)c3ccccc3)c12]

7-(3,5-Dimethyl-4-isoxazolyl)-8-(methyloxy)-1-[(1R)-1-phenylethyl]-1,3-dihydro-2H-imidazo[4,5-c]quinolin-2-one (for a preparation see Intermediate 11) (0.33 g, 0.796 mmol) was heated in a mixture of POCl₃ (1 ml, 10.73 mmol) and PCl₅ (0.166 g, 0.796 mmol) at 120° C. for 5 h, then cooled and allowed to stand at room temperature overnight. The mixture was evaporated in vacuo and then the residue suspended in toluene and evaporated to a brown gum. This was dissolved in DCM (20 ml) and washed with saturated sodium hydrogen carbonate solution, then the organic layer was loaded onto a 25 g silica cartridge. The column was eluted with EtOAc/cyclohexane (0-100%) and the product-containing fractions evaporated in vacuo to give 2-chloro-7-(3,5-dimethyl-4-isoxazolyl)-8-(methyloxy)-1-[(1R)-1-phenylethyl]-1H-imidazo[4,5-c]quinoline (31 mg, 0.072 mmol, 8.99% yield) as a beige glass. LCMS (formate) Rt 1.05 min, MH+ 433.

Intermediate 13

7-(3,5-dimethyl-4-isoxazolyl)-6-(methyloxy)-4-[(tetrahydro-2H-pyran-4-ylmethyl)amino]-3-quinolinecarboxamide

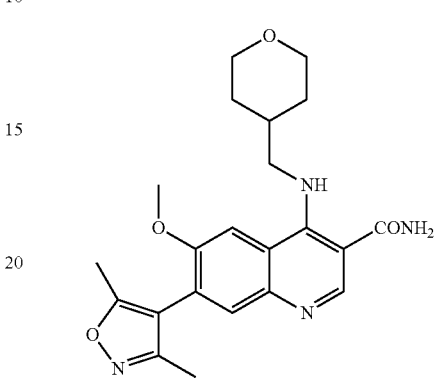

4-Chloro-7-(3,5-dimethyl-4-isoxazolyl)-6-(methyloxy)-3-quinolinecarboxamide (for a preparation see Intermediate 9) (1.890 g, 5.70 mmol) was dissolved in NMP (5 ml), DIPEA (2.487 ml, 14.24 mmol) was added followed by (tetrahydro-2H-pyran-4-yl)methanamine (0.82 g, 7.12 mmol) and the mixture was heated at 120° C. for 3 h, then cooled and the brown solution loaded onto a 70 g SCX-2 cartridge, the column washed with methanol (200 ml) and then eluted with 2M methanolic ammonia (100 ml) and methanol (100 ml). The eluant was evaporated in vacuo to give a brown solid. This was triturated with EtOAc (30 ml) and the solid collected by filtration to give 7-(3,5-dimethyl-4-isoxazolyl)-6-(methyloxy)-4-[(tetrahydro-2H-pyran-4-ylmethyl)amino]-3-quinolinecarboxamide (1.58 g, 3.85 mmol, 54.1% yield) as brown solid. LCMS (formate) Rt 0.64, MH+ 411

Intermediate 14

7-(3,5-dimethyl-4-isoxazolyl)-8-(methyloxy)-1-(tetrahydro-2H-pyran-4-ylmethyl)-1,3-dihydro-2H-imidazo[4,5-c]quinolin-2-one

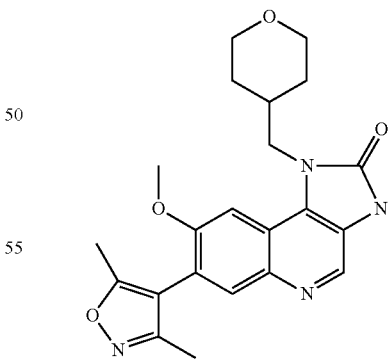

7-(3,5-Dimethyl-4-isoxazolyl)-6-(methyloxy)-4-[(tetrahydro-2H-pyran-4-ylmethyl)amino]-3-quinolinecarboxamide (for a preparation see Intermediate 13) (1.50 g, 3.65 mmol) was suspended in methanol (50 ml) and potassium hydroxide (0.308 g, 5.48 mmol) was added. the mixture was stirred for 20 min, then cooled in an ice bath and iodobenzene diacetate (1.530 g, 4.75 mmol) was added, then the mixture stirred for a further 2 h at 0° C. A fine beige precipitate appeared and after a further 30 min of stirring, the mixture was filtered and the solid washed with methanol (5 ml), then dried in the vacuum oven to give 7-(3,5-dimethyl-4-isoxazolyl)-8-(methyloxy)-1-(tetrahydro-2H-pyran-4-ylmethyl)-1,3-dihydro-2H-imidazo[4,5-c]quinolin-2-one (1.400 g, 3.43 mmol, 94% yield) as beige powder. LCMS (formate) Rt 0.65 min, MH+ 409

Intermediate 15

2-chloro-7-(3,5-dimethyl-4-isoxazolyl)-8-(methyloxy)-1-(tetrahydro-2H-pyran-4-ylmethyl)-1H-imidazo[4,5-c]quinoline

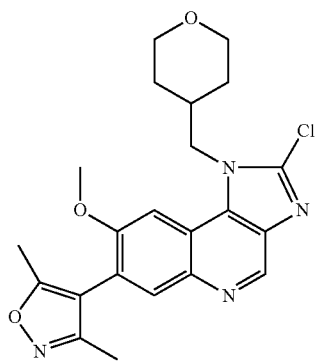 [SMILES: COc1cc2c(cc1-c1c(C)noc1C)ncc1nc(Cl)n(CC3CCOCC3)c12]

7-(3,5-Dimethyl-4-isoxazolyl)-8-(methyloxy)-1-(tetrahydro-2H-pyran-4-ylmethyl)-1,3-dihydro-2H-imidazo[4,5-c]quinolin-2-one (for a preparation see Intermediate 14) (220 mg, 0.539 mmol) was dissolved in POCl$_3$ (2 ml, 21.46 mmol), PCl$_5$ (0.2 g, 0.960 mmol) was added and the mixture was heated at 120° C. for 24 h. The reaction mixture was evaporated in vacuo to give a beige solid. This was dissolved in DCM (3 ml) and loaded onto a 25 g silica column, then eluted with 0-10% 2M methanolic ammonia/DCM (25 column volumes) and product containing fractions were evaporated in vacuo to give 2-chloro-7-(3,5-dimethyl-4-isoxazolyl)-8-(methyloxy)-1-(tetrahydro-2H-pyran-4-ylmethyl)-1H-imidazo[4,5-c]quinoline (14.2 mg, 0.033 mmol, 6.18% yield) as beige solid. LCMS (formate) Rt 0.81 min, MH+ 427.

Intermediate 16

7-(3,5-dimethylisoxazol-4-yl)-6-methoxy-3-nitro-N-((tetrahydro-2H-pyran-4-yl)methyl)quinolin-4-amine

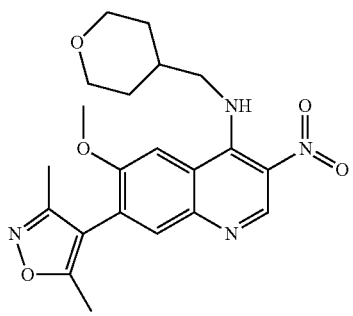 [SMILES: COc1cc2c(NCC3CCOCC3)c([N+](=O)[O-])cnc2cc1-c1c(C)noc1C]

4-Chloro-7-(3,5-dimethyl-4-isoxazolyl)-6-(methyloxy)-3-nitroquinoline (for a preparation see Intermediate 8) (1.06 g, 3.18 mmol) was dissolved in NMP (5 ml), then DIPEA (0.56 ml, 3.18 mmol) and (tetrahydro-2H-pyran-4-yl)methanamine (0.75 g, 6.51 mmol) were added at room temperature. The reaction mixture immediately changed colour and within 5 minutes, a thick yellow precipitate was formed. The mixture was stirred for 20 min, then diluted with water (30 ml) and stirred for 10 min. The precipitate was collected by filtration and washed with water (2×20 ml), then dried in vacuo to give 7-(3,5-dimethylisoxazol-4-yl)-6-methoxy-3-nitro-N-((tetrahydro-2H-pyran-4-yl)methyl)quinolin-4-amine (1.22 g, 2.96 mmol, 93% yield) as a bright yellow solid. LCMS (formate) Rt 0.88 min, MH+ 413

Intermediate 17

7-(3,5-dimethyl-4-isoxazolyl)-6-(methyloxy)-N$^4$-(tetrahydro-2H-pyran-4-ylmethyl)-3,4-quinolinediamine

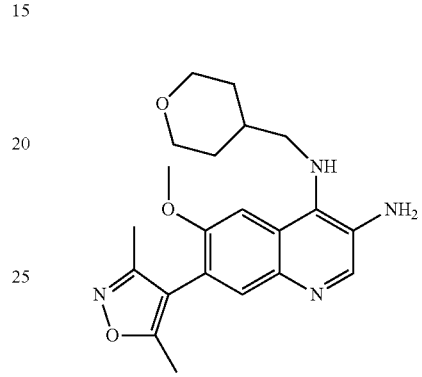

7-(3,5-Dimethylisoxazol-4-yl)-6-methoxy-3-nitro-N-((tetrahydro-2H-pyran-4-yl)methyl)quinolin-4-amine (for a preparation see Intermediate 16) (1.2 g, 2.91 mmol) was dissolved in a mixture of ethyl acetate (60 ml) and methanol (10 ml) and hydrogenated over Pd/C (0.310 g, 2.91 mmol, 5% w/w, 50% water, Type E101 NO/W) for 24 h at atmospheric pressure under a hydrogen burette. The mixture was filtered and evaporated and the residue was dissolved in DCM (3 ml) and loaded onto a 50 g silica column, then eluted with 0-15% 2M methanolic ammonia/DCM and product containing fractions evaporated in vacuo to give 7-(3,5-dimethylisoxazol-4-yl)-6-methoxy-N4-((tetrahydro-2H-pyran-4-yl)methyl)quinoline-3,4-diamine (0.45 g, 1.177 mmol, 40.4% yield) as a pale yellow solid. LCMS (formate) Rt 0.68 min, MH+ 384

Intermediate 18

7-(3,5-dimethyl-4-isoxazolyl)-N-[1-methyl-2-(methyloxy)ethyl]-6-(methyloxy)-3-nitro-4-quinolinamine

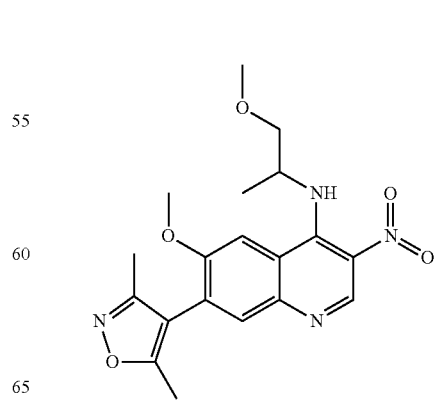

1-(Methyloxy)-2-propanamine (0.35 g) and 4-chloro-7-(3,5-dimethyl-4-isoxazolyl)-6-(methyloxy)-3-nitroquinoline (for a preparation see Intermediate 8) (0.74 g, 2.217 mmol) were dissolved in a mixture of triethylamine (0.30 ml, 2.2 mmol) and NMP (3 ml) and the solution was allowed to stand for 30 min at room temperature, then diluted with water (20 ml) and the resulting suspension stirred for 20 min, then filtered and the resulting solid washed with water (10 ml) and dried in the vacuum oven at 50° C. to give the title compound as bright yellow solid. (0.80 g, 2.070 mmol, 93% yield). LCMS (formate) Rt 0.97 MH+ 387

Intermediate 19

7-(3,5-dimethyl-4-isoxazolyl)-N$^4$-[1-methyl-2-(methyloxy)ethyl]-6-(methyloxy)-3,4-quinolinediamine

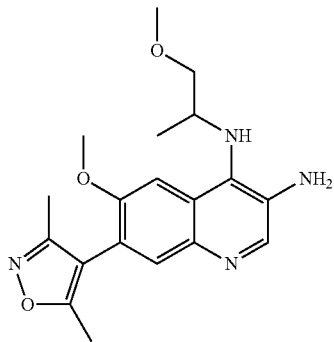 [SMILES: COCC(C)Nc1c(N)cnc2cc(-c3c(C)noc3C)c(OC)cc12]

7-(3,5-dimethylisoxazol-4-yl)-6-methoxy-N-(1-methoxypropan-2-yl)-3-nitroquinolin-4-amine (0.80 g, 2.070 mmol) was dissolved in EtOAc (120 ml) and hydrogenated using a flow hydrogenation apparatus (H Cube™, settings: full hydrogen, atmospheric pressure, 1 ml/min flow rate). The eluant was evaporated in vacuo to give the title compound as an orange gum (0.73 g, 99%). LCMS (formate) Rt 0.73 min, MH+ 357.

Intermediate 20

7-(3,5-dimethyl-4-isoxazolyl)-6-(methyloxy)-3-nitro-N-(2-pyridinylmethyl)-4-quinolinamine

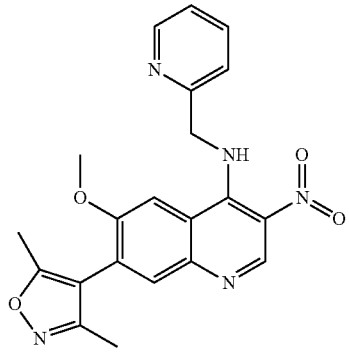

A mixture of 4-chloro-7-(3,5-dimethyl-4-isoxazolyl)-6-(methyloxy)-3-nitroquinoline (1.5 g, 3.5 mmol) and 2-(aminomethyl)pyridine (1.46 g, 13.5 mmol) in dioxan (10 ml) was stirred at room temperature for 2 h. The reaction mixture was cooled and the solvent was evaporated. The residue was chromatographed [50-100% ethyl acetate/cyclohexane] to give the title compound as a yellow solid (1.5 g, 3.70 mmol, 82% yield). LCMS (formate) Rt 0.86 min, MH+ 406.

Intermediate 21

7-(3,5-dimethyl-4-isoxazolyl)-6-(methyloxy)-N$^4$-(2-pyridinylmethyl)-3,4-quinolinediamine

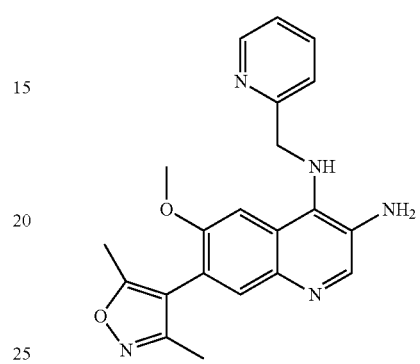

10% palladium on carbon, 50% water paste, (300 mg, 20% wt) was added to a solution of 7-(3,5-dimethyl-4-isoxazolyl)-6-(methyloxy)-3-nitro-N-(2-pyridinylmethyl)-4-quinolinamine (1.5 g, 3.70 mmol) in ethyl acetate (90 ml) and ethanol (10 ml). The reaction mixture was stirred in an atmosphere of hydrogen for 3 h. The reaction mixture was filtered through Celite™. The solvent was evaporated from the filtrate. The residue was chromatographed [5% methanol/DCM] to give the title compound as a brown oil (1.23 g, 3.28 mmol, 89% yield). LCMS (formate) Rt 0.63 min, MH+ 376

Intermediate 22

7-(3,5-dimethyl isoxazol-4-yl)-6-methoxy-N$^4$-(1-(1-methyl-1H-pyrazol-4-yl)ethyl)quinoline-3,4-diamine

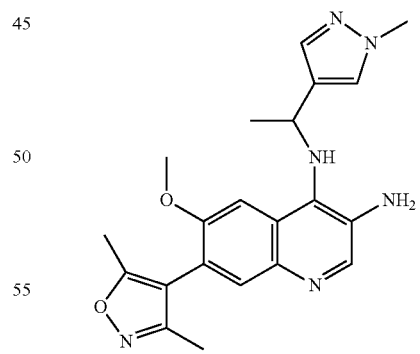

7-(3,5-Dimethylisoxazol-4-yl)-6-methoxy-N-(1-(1-methyl-1H-pyrazol-4-yl)ethyl)-3-nitroquinolin-4-amine (0.20 g, 0.473 mmol, for preparation see Intermediate 23) was dissolved in EtOAc (80 ml) and hydrogenated using a flow hydrogenator (H-Cube™ settings: full Hydrogen mode, atmospheric pressure, 20° C., 1 ml/min flow rate) to give an orange solution. The eluant was evaporated in vacuo to give 7-(3,5-dimethylisoxazol-4-yl)-6-methoxy-N4-(1-(1-methyl-1H-pyrazol-4-yl)ethyl)quinoline-3,4-diamine (0.17 g, 0.433 mmol, 91% yield) as an orange gum which was used without further purification. LCMS (formate) Rt 0.66 min, MH+ 393.

Intermediate 23

7-(3,5-Dimethyl isoxazol-4-yl)-6-methoxy-N-(1-(1-methyl-1H-pyrazol-4-yl)ethyl)-3-nitroquinolin-4-amine

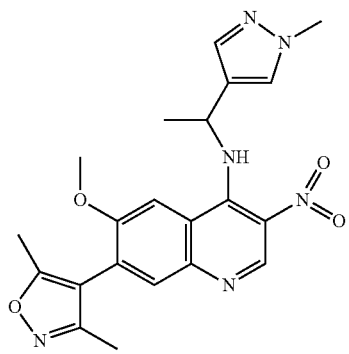 [SMILES: COc1cc2c(NC(C)c3cnn(C)c3)c([N+](=O)[O-])cnc2cc1-c1c(C)noc1C]

4-(4-Chloro-6-methoxy-3-nitroquinolin-7-yl)-3,5-dimethylisoxazole (200 mg, 0.599 mmol, for preparation see Intermediate 8) and [1-(1-methyl-1H-pyrazol-4-yl)ethyl]amine (113 mg, 0.9 mmol) were heated in a mixture of DIPEA (0.324 ml, 1.858 mmol) and NMP (15 ml) at 120° C. for 4 h. The reaction mixture was cooled to room temperature, diluted with water (300 ml) and extracted with EtOAc (2×200 ml). The combined organic phase was washed with water (300 ml) and brine (200 ml), dried with sodium sulphate and evaporated. The resulting gum was dissolved in DCM (3 ml) loaded onto a 100 g silica cartridge and eluted with 2M methanolic ammonia/DCM (0-12%). The product-containing fractions were evaporated in vacuo to give 7-(3,5-dimethylisoxazol-4-yl)-6-methoxy-N-(1-(1-methyl-1H-pyrazol-4-yl)ethyl)-3-nitroquinolin-4-amine (0.21 g, 0.497 mmol, 83% yield) which was used in the subsequent step without further purification. LCMS (formate) Rt 0.87 min, MH+ 423.

Intermediate 24

7-(3,5-dimethylisoxazol-4-yl)-6-methoxy-3-nitro-N—((R)-1-(pyridin-2-yl)ethyl)quinolin-4-amine

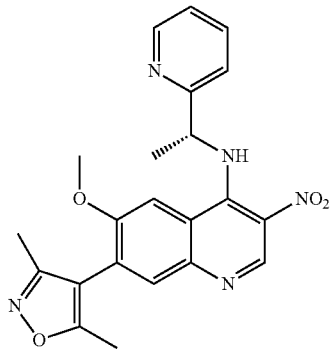 [SMILES: COc1cc2c(N[C@H](C)c3ccccn3)c([N+](=O)[O-])cnc2cc1-c1c(C)noc1C]

To a solution of 4-(4-chloro-6-methoxy-3-nitroquinolin-7-yl)-3,5-dimethylisoxazole (for a preparation, see Intermediate 8) (1 g, 3.00 mmol) in 1,4-dioxane (6.5 mL) was added (R)-1-(pyridin-2-yl)ethanamine (0.549 g, 4.49 mmol) and the mixture stirred at room temperature for 5 h. A further portion of (R)-1-(pyridin-2-yl)ethanamine (0.255 g, 2.25 mmol) was added and the mixture stirred at room temperature overnight. The solvent was removed under reduced pressure and the residue purified by chromatography (50 g column, cyclohexane/EtOAc gradient) to give 7-(3,5-dimethylisoxazol-4-yl)-6-methoxy-3-nitro-N—((R)-1-(pyridin-2-yl)ethyl)quinolin-4-amine (1.15 g, 2.74 mmol, 92% yield) as an orange solid. LCMS: (Formate, 2 min), Rt 0.98 mins, MH+ 420.

Intermediate 25

7-(3,5-dimethylisoxazol-4-yl)-6-methoxy-$N^4$—((R)-1-(pyridin-2-yl)ethyl)quinoline-3,4-diamine

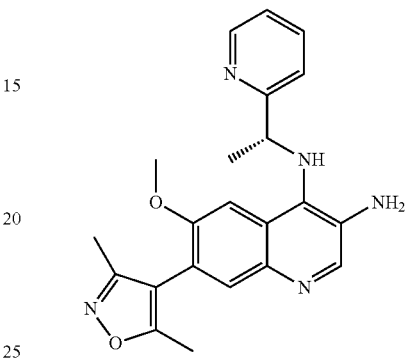

To a suspension of 7-(3,5-dimethylisoxazol-4-yl)-6-methoxy-3-nitro-N—((R)-1-(pyridin-2-yl)ethyl)quinolin-4-amine (Intermediate 24) (1.05 g, 2.503 mmol) in EtOH (20 mL) was added tin(II) chloride (1.66 g, 8.76 mmol) and the mixture stirred at 40° C. for 2.5 h. The reaction mixture was basified to pH 12 using 2M aq. sodium hydroxide solution. Water (30 mL) was added and the aqueous suspension extracted with DCM (3×30 mL). The organic layers were combined, dried by passing through a hydrophobic frit and concentrated to dryness under a stream of nitrogen. The resulting residue was purified by chromatography (100 g column, 2M methanolic ammonia gradient) to give 7-(3,5-dimethylisoxazol-4-yl)-6-methoxy-$N^4$—((R)-1-(pyridin-2-yl)ethyl)quinoline-3,4-diamine (543 mg, 1.39 mmol, 56% yield) as a dark brown gum.
LCMS: (Formate, 2 min) Rt 0.69 mins, MH+ 390.

Example 1

2-({7-(3,5-dimethyl-4-isoxazolyl)-8-(methyloxy)-1-[(1R)-1-phenylethyl]-1H-imidazo[4,5-c]quinolin-2-yl}amino)ethanol

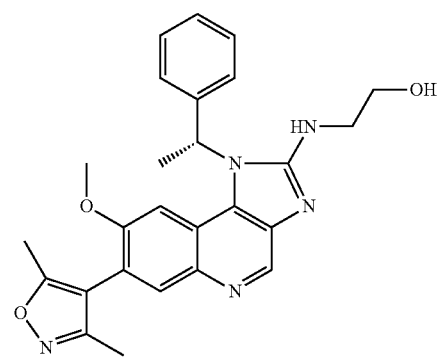 [SMILES: COc1cc2c(cc1-c1c(C)noc1C)ncc1nc(NCCO)n([C@H](C)c3ccccc3)c12]

2-Chloro-7-(3,5-dimethyl-4-isoxazolyl)-8-(methyloxy)-1-[(1R)-1-phenylethyl]-1H-imidazo[4,5-c]quinoline (for a preparation see Intermediate 12) (30 mg, 0.035 mmol) was dissolved in NMP (0.5 ml), ethanolamine (30 mg) was added and the mixture was heated at 150° C. for 30 min, then cooled, added to water (10 ml) and extracted with EtOAc (10 ml). The organic phase was washed with water (2×10 ml), dried and evaporated. The residue was dissolved in DCM (2 ml), loaded onto a 10 g silica column and eluted with 2M methanolic ammonia/DCM (0-10%). The product-containing fractions were evaporated in vacuo to give 2-({7-(3,5-dimethyl-4-isoxazolyl)-8-(methyloxy)-1-[(1R)-1-phenylethyl]-1H-imidazo[4,5-c]quinolin-2-yl}amino)ethanol (8.4 mg, 0.018 mmol, 53.0% yield) as a light brown glass. LCMS (formate) Rt 0.77 min, MH+ 458

1H NMR (400 MHz, CDCl$_3$) δH 9.0 (1H, s), 7.88 (H, s), 7.35-7.45 (6H, m), 6.95 (1H, br s), 6.12 (1H, br s), 4.60 (1H, m), 3.80-3.84 (2H, m), 3.62-3.58 (2H, m), 3.45 (3H, s), 2.33 (3H, s), 2.15 (3H, s), 2.07 (3H, d)

Example 2

2-{[7-(3,5-dimethyl-4-isoxazolyl)-8-(methyloxy)-1-(tetrahydro-2H-pyran-4-ylmethyl)-1H-imidazo[4,5-c]quinolin-2-yl]amino}ethanol

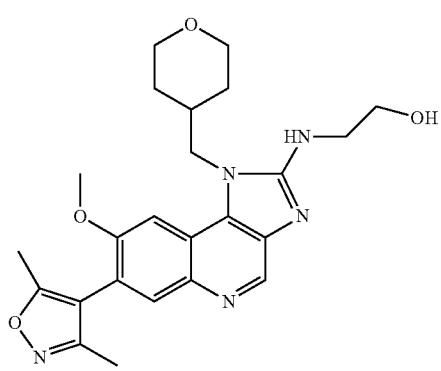 [SMILES: COc1cc2c(cc1-c1c(C)noc1C)ncc1nc(NCCO)n(CC3CCOCC3)c12]

2-Chloro-7-(3,5-dimethyl-4-isoxazolyl)-8-(methyloxy)-1-(tetrahydro-2H-pyran-4-ylmethyl)-1H-imidazo[4,5-c]quinoline (for a preparation see Intermediate 15) (14 mg, 0.033 mmol) and ethanolamine (0.020 ml, 0.327 mmol) were dissolved in NMP (2 ml) and heated at 180° C. in the microwave for 1 h, then cooled and loaded onto a 10 g SCX-2 cartridge, washing with methanol (30 ml). The cartridge was then eluted with 2M methanolic ammonia (30 ml) and the eluant evaporated in vacuo to give a sparingly soluble brown gum. This was dissolved in DMSO (1 ml) and purified by MDAP (formate) to give 2-{[7-(3,5-dimethyl-4-isoxazolyl)-8-(methyloxy)-1-(tetrahydro-2H-pyran-4-ylmethyl)-1H-imidazo[4,5-c]quinolin-2-yl]amino}ethanol (0.80 mg, 1.772 μmol, 5.40% yield) as a pale yellow glass. LCMS (formate) Rt 0.62 min, MH+ 452

$^1$H NMR (400 MHz, MeOD) δH 8.59 (1H, s), 7.82 (1H, s), 7.43 (1H, s), 4.32 (2H, d), 3.93 (3H, s), 3.74 (2H, t), 3.58 (2H, dd), 3.08 (2H, t), 2.86 (2H, dt), 2.27 (1H, m), 2.21 (3H, s), 2.04 (3H, s), 1.96 (2H, dd), 1.73 (2H, dt)

Example 3

7-(3,5-dimethyl-4-isoxazolyl)-8-(methyloxy)-1-(tetrahydro-2H-pyran-4-ylmethyl)-1H-imidazo[4,5-c]quinolin-2-amine

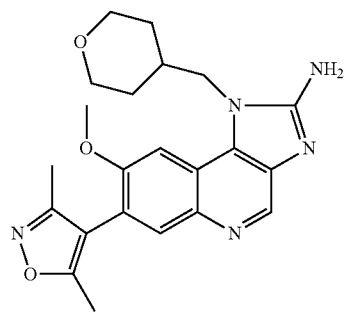 [SMILES: COc1cc2c(cc1-c1c(C)noc1C)ncc1nc(N)n(CC3CCOCC3)c12]

7-(3,5-Dimethylisoxazol-4-yl)-6-methoxy-N4-((tetrahydro-2H-pyran-4-yl)methyl)quinoline-3,4-diamine (for a preparation see Intermediate 17) (32 mg, 0.084 mmol) was dissolved in ethanol (3 ml) and cyanogen bromide (8.86 mg, 0.084 mmol) was added, then the mixture stirred overnight at room temperature. The reaction mixture was evaporated to dryness, the residue dissolved in DMSO (1 ml) and purified by MDAP (formate) to give 7-(3,5-dimethylisoxazol-4-yl)-8-methoxy-1-((tetrahydro-2H-pyran-4-yl)methyl)-1H-imidazo[4,5-c]quinolin-2-amine (4.5 mg, 0.011 mmol, 13.2% yield) as a yellow glass. LCMS (formate) Rt 0.65 min, MH+ 408

$^1$H NMR (400 MHz, CDCl$_3$) 9.05 (1H, s), 8.10 (1H, s), 7.38 (1H, s), 6.33 (2H, br s), 4.35 (2H, d), 4.05 (2H, d), 3.93 (3H, s), 3.30 (2H, m), 2.40 (1H, m), 2.35 (3H, s), 2.21 (3H, s), 1.65 (4H, m)

Similarly prepared were Examples 4 and 5

Example 4

7-(3,5-dimethyl-4-isoxazolyl)-8-(methyloxy)-1-(2-pyridinylmethyl)-1H-imidazo[4,5-c]quinolin-2-amine

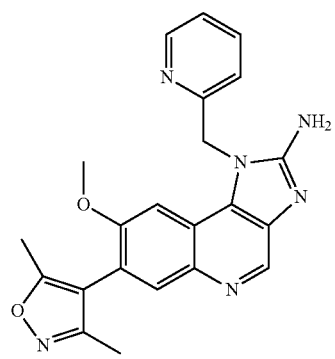 [SMILES: COc1cc2c(cc1-c1c(C)noc1C)ncc1nc(N)n(Cc3ccccn3)c12]

From 7-(3,5-dimethyl-4-isoxazolyl)-6-(methyloxy)-N$^4$-(2-pyridinylmethyl)-3,4-quinolinediamine (for a preparation see Intermediate 17) (35 mg) and cyanogen bromide (10 mg)

to give the title compound as beige solid (12 mg, 32%). LCMS (formate) Rt 0.61 min, MH+ 401

Example 5

7-(3,5-dimethyl-4-isoxazolyl)-1-[1-methyl-2-(methyloxy)ethyl]-8-(methyloxy)-1H-imidazo[4,5-c]quinolin-2-amine

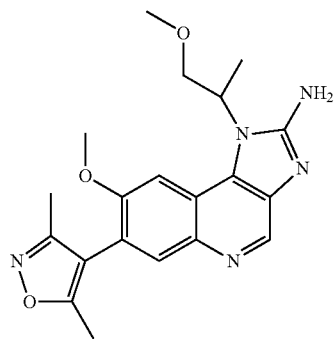 [SMILES: COCC(C)n1c(N)nc2cnc3cc(-c4c(C)noc4C)c(OC)cc3c21]

From 7-(3,5-dimethyl-4-isoxazolyl)-N4-[1-methyl-2-(methyloxy)ethyl]-6-(methyloxy)-3,4-quinolinediamine (for a preparation see Intermediate 17) (70 mg) and cyanogen bromide (20 mg) to give the title compound as beige solid (23 mg, 30%). LCMS (formate) Rt 0.67 min, MH+ 382

Example 6

7-(3,5-dimethyl-4-isoxazolyl)-N-ethyl-8-(methyloxy)-1-(tetrahydro-2H-pyran-4-ylmethyl)-1H-imidazo[4,5-c]quinolin-2-amine

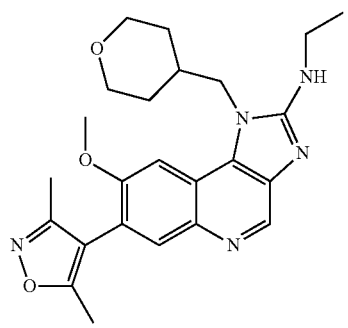 [SMILES: CCNc1nc2cnc3cc(-c4c(C)noc4C)c(OC)cc3c2n1CC1CCOCC1]

7-(3,5-Dimethylisoxazol-4-yl)-6-methoxy-N4-((tetrahydro-2H-pyran-4-yl)methyl)quinoline-3,4-diamine (for a preparation see Intermediate 17) (100 mg, 0.261 mmol) was dissolved in methanol and ethyl isothiocyanate (45.6 mg, 0.523 mmol) was added. The mixture was heated at 50° C. for 6 h, cooled and evaporated in vacuo to give a beige solid residue. This was re-dissolved in THF (5 ml) and EDC (100 mg, 0.523 mmol) was added, then the mixture heated at 60° C. overnight. The solvent was evaporated in vacuo and the residue dissolved in DCM (10 ml) and washed with water (10 ml), the organic layer dried and evaporated and the residue dissolved in DCM (2 ml) and loaded onto a 10 g silica column, then eluted with 2M methanolic ammonia/DCM (0-10%) and product-containing fractions evaporated in vacuo to give 7-(3,5-dimethylisoxazol-4-yl)-N-ethyl-8-methoxy-1-((tetrahydro-2H-pyran-4-yl)methyl)-1H-imidazo[4,5-c]quinolin-2-amine (37 mg, 0.085 mmol, 32.5% yield) as a colourless glass. LCMS (formate) Rt 0.71 min, MH+ 436

$^1$H NMR (400 MHz, CDCl$_3$) δH 9.05 (1H, s), 7.95 (1H, s), 7.32 (1H, s), 4.39 (1H, t), 4.21 (2H, d), 4.00 (2H, dd), 3.91 (3H, s), 3.69 (2H, tt), 3.32 (2H, dt), 2.38 (1H, m), 2.35 (3H, s), 2.22 (3H, s), 1.52-1.70 (4H, m), 1.35 (3H, t)

Similarly prepared were the following examples.

Example 7

7-(3,5-dimethylisoxazol-4-yl)-N-ethyl-8-methoxy-1-(1-methoxypropan-2-yl)-1H-imidazo[4,5-c]quinolin-2-amine

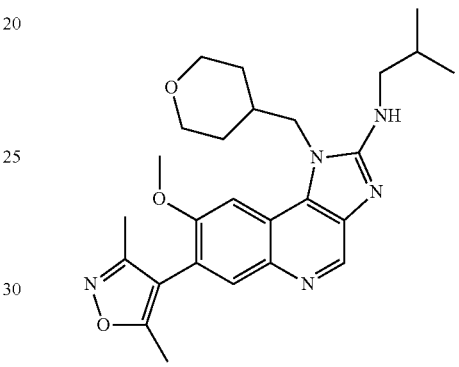

From 7-(3,5-dimethylisoxazol-4-yl)-6-methoxy-N4-((tetrahydro-2H-pyran-4-yl)methyl)quinoline-3,4-diamine (for a preparation see Intermediate 17) (70 mg) and 1-isothiocyanato-2-methylpropane (50 mg) to give the title compound as a beige solid (52 mg, 61%). LCMS (formate) Rt 0.79 min, MH+ 464

Example 8

N1-(7-(3,5-dimethylisoxazol-4-yl)-8-methoxy-1-((tetrahydro-2H-pyran-4-yl)methyl)-1H-imidazo[4,5-c]quinolin-2-yl)ethane-1,2-diamine

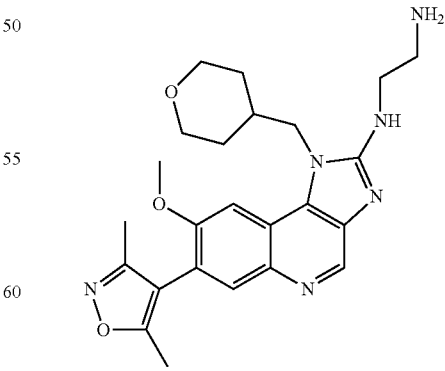

From 7-(3,5-dimethylisoxazol-4-yl)-6-methoxy-N4-((tetrahydro-2H-pyran-4-yl)methyl)quinoline-3,4-diamine (for a preparation see Intermediate 17) (70 mg) and 1,1-dimethylethyl (2-isothiocyanatoethyl)carbamate (50 mg). The crude product isolated was treated with TFA (2 ml) in DCM (10 ml), the mixture stirred for 1 h, then evaporated in vacuo. The residue was dissolved in DMSO (1 ml) and purified by MDAP (HpH method) to give the title compound as a beige solid (26 mg, 31%). LCMS (HpH) Rt 0.73 min, MH+ 451

Example 9

7-(3,5-dimethyl-4-isoxazolyl)-8-(methyloxy)-N-[2-(4-morpholinyl)ethyl]-1-(tetrahydro-2H-pyran-4-ylmethyl)-1H-imidazo[4,5-c]quinolin-2-amine

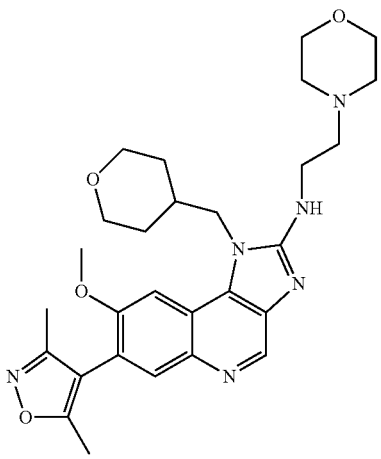 [SMILES: COc1cc2c(cc1-c1c(C)noc1C)ncc1nc(NCCN3CCOCC3)n(CC3CCOCC3)c12]

From 7-(3,5-dimethylisoxazol-4-yl)-6-methoxy-N4-((tetrahydro-2H-pyran-4-yl)methyl)quinoline-3,4-diamine (for a preparation see Intermediate 17) (70 mg) and 4-(2-isothiocyanatoethyl)morpholine (50 mg) to give the title compound as beige solid (57 mg, 60%). LCMS (formate) Rt 0.51 min, MH+ 521

Example 10

7-(3,5-dimethyl-4-isoxazolyl)-8-(methyloxy)-N-[2-(methyloxy)ethyl]-1-(tetrahydro-2H-pyran-4-ylmethyl)-1H-imidazo[4,5-c]quinolin-2-amine

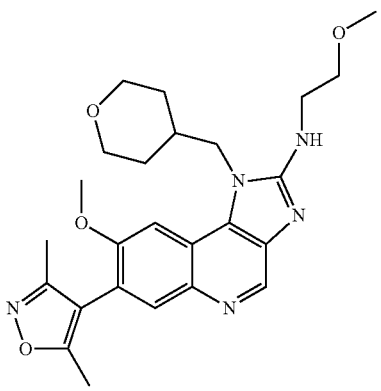 [SMILES: COCCNc1nc2cnc3cc(-c4c(C)noc4C)c(OC)cc3c2n1CC1CCOCC1]

From 7-(3,5-dimethylisoxazol-4-yl)-6-methoxy-N4-((tetrahydro-2H-pyran-4-yl)methyl)quinoline-3,4-diamine (for a preparation see Intermediate 17) (70 mg) and 1-isothiocyanato-2-(methyloxy)ethane (50 mg) to give the title compound as beige solid (55 mg, 65%). LCMS (formate) Rt 0.68 min, MH+ 466

Example 11

7-(3,5-dimethyl-4-isoxazolyl)-N-ethyl-1-[1-methyl-2-(methyloxy)ethyl]-8-(methyloxy)-1H-imidazo[4,5-c]quinolin-2-amine

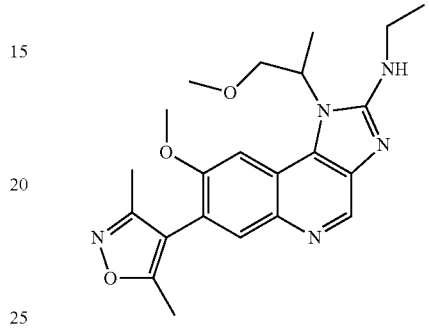

From 7-(3,5-dimethylisoxazol-4-yl)-6-methoxy-N4-(1-methoxypropan-2-yl)quinoline-3,4-diamine (for a preparation see Intermediate 17) (70 mg) and isothiocyanatoethane (50 mg) to give the title compound as beige solid (42 mg, 52%). LCMS (formate) Rt 0.78 min, MH+ 410

Example 12

N-[7-(3,5-dimethyl-4-isoxazolyl)-1-[1-methyl-2-(methyloxy)ethyl]-8-(methyloxy)-1H-imidazo[4,5-c]quinolin-2-yl]-1,2-ethanediamine

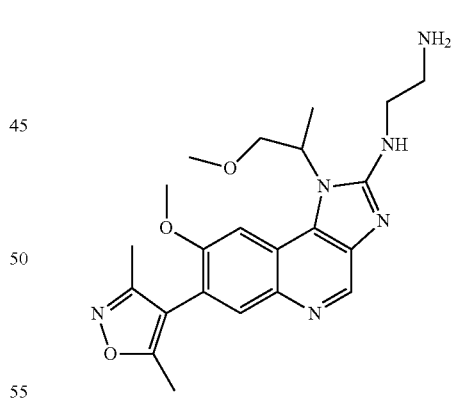

From 7-(3,5-dimethylisoxazol-4-yl)-6-methoxy-N4-(1-methoxypropan-2-yl)quinoline-3,4-diamine (70 mg) and 1,1-dimethylethyl (2-isothiocyanatoethyl)carbamate (50 mg). The crude product isolated was treated with TFA (2 ml) in DCM (10 ml), the mixture stirred for 1 h, then evaporated in vacuo. The residue was dissolved in DMSO (1 ml) and purified by MDAP (HpH) to give the title compound as a beige solid (4.5 mg, 4%).

LCMS (HpH) Rt 0.77 min, MH+ 425

Example 13

7-(3,5-dimethyl-4-isoxazolyl)-1-[1-methyl-2-(methyloxy)ethyl]-8-(methyloxy)-N-[2-(4-morpholinyl)ethyl]-1H-imidazo[4,5-c]quinolin-2-amine

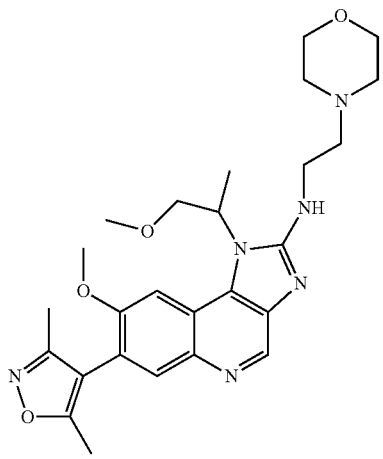 [SMILES: COCC(C)n1c(NCCN2CCOCC2)nc2cnc3cc(-c4c(C)noc4C)c(OC)cc3c21]

From 7-(3,5-dimethylisoxazol-4-yl)-6-methoxy-N4-(1-methoxypropan-2-yl)quinoline-3,4-diamine (for a preparation see Intermediate 19) (70 mg) and 4-(2-isothiocyanatoethyl)morpholine (50 mg) to give the title compound as beige solid (45 mg, 46%). LCMS (formate) Rt 0.56 min, MH+ 495

Example 14

7-(3,5-dimethyl-4-isoxazolyl)-1-[1-methyl-2-(methyloxy)ethyl]-8-(methyloxy)-N-[2-(methyloxy)ethyl]-1H-imidazo[4,5-c]quinolin-2-amine

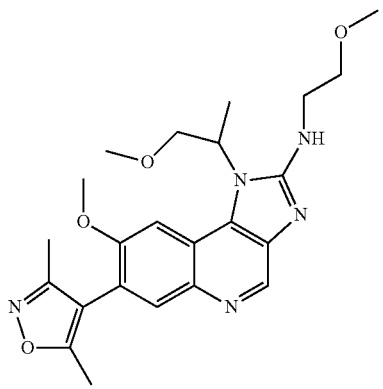 [SMILES: COCCNc1nc2cnc3cc(-c4c(C)noc4C)c(OC)cc3c2n1C(C)COC]

From 7-(3,5-dimethylisoxazol-4-yl)-6-methoxy-N4-(1-methoxypropan-2-yl)quinoline-3,4-diamine (for a preparation see Intermediate 19) (70 mg) and 1-isothiocyanato-2-(methyloxy)ethane (50 mg) to give the title compound as beige solid (41 mg, 47%). LCMS (formate) Rt 0.56 min, MH+ 440.

Example 15

7-(3,5-dimethyl-4-isoxazolyl)-8-(methyloxy)-N-[2-(methyloxy)ethyl]-1-(2-pyridinylmethyl)-1H-imidazo[4,5-c]quinolin-2-amine

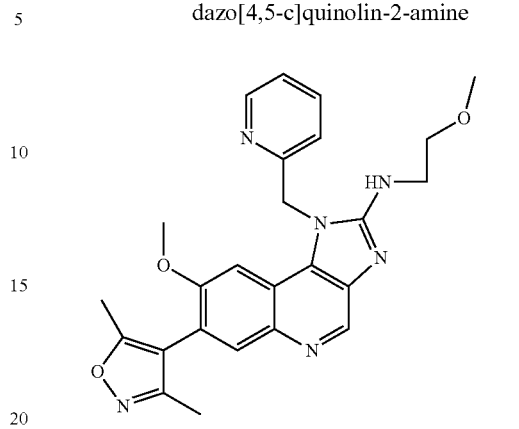

7-(3,5-Dimethylisoxazol-4-yl)-6-methoxy-N4-(pyridin-2-ylmethyl)quinoline-3,4-diamine (35 mg, 0.093 mmol) was dissolved in ethanol (5 ml) and 2-methoxyethyl isothiocyanate (22 mg, 0.186 mmol) was added, then the solution was heated at 60° C. for 3 h, cooled and evaporated in vacuo. The residue was dissolved in THF (5.0 ml) and EDC (35.7 mg, 0.186 mmol) was added, then the solution was heated at 60° C. for 3 h, cooled and evaporated in vacuo and the residue purified by MDAP (formate) to give 7-(3,5-dimethylisoxazol-4-yl)-8-methoxy-N-(2-methoxyethyl)-1-(pyridin-2-ylmethyl)-1H-imidazo[4,5-c]quinolin-2-amine (25 mg, 0.055 mmol, 58.5% yield) as a beige solid.
LCMS (formate) Rt 0.66 min, MH+ 459

Example 16

7-(3,5-dimethyl-4-isoxazolyl)-8-(methyloxy)-2-(4-morpholinyl)-1-[(1R)-1-phenylethyl]-1H-imidazo[4,5-c]quinoline

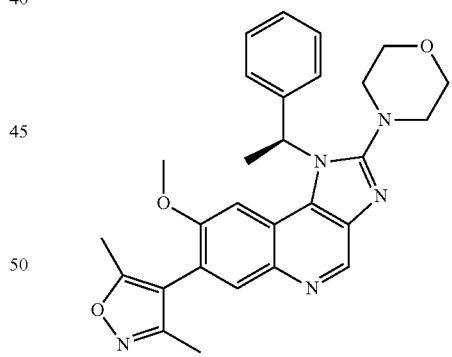

7-(3,5-Dimethyl-4-isoxazolyl)-8-(methyloxy)-1-[(1R)-1-phenylethyl]-1,3-dihydro-2H-imidazo[4,5-c]quinolin-2-one (for a preparation see Intermediate 11) (0.16 g, 0.386 mmol) was dissolved in POCl₃ (1 ml, 10.73 mmol) and heated at 100° C. for 3 days. The reaction mixture was evaporated in vacuo to give a black gum. The residue was dissolved in NMP (2 ml) and morpholine (2 ml, 22.96 mmol) was added, then the solution was heated in the microwave at 150° C. for 1 h. The reaction mixture was loaded onto a 20 g SCX-2 cartridge and washed through with methanol (40 ml), then eluted with 2M methanolic ammonia and the eluant evaporated in vacuo to give an amber oil. This was dissolved in DMSO (1 ml) and purified by MDAP (HpH) to give 7-(3,5-dimethyl-4-isoxazolyl)-8-(methyloxy)-2-(4-morpholinyl)-1-[(1R)-1-phe-

Example 17

7-(3,5-dimethyl-4-isoxazolyl)-8-(methyloxy)-1-[(1R)-1-phenylethyl]-2-(1-piperidinyl)-1H-imidazo[4,5-c]quinoline

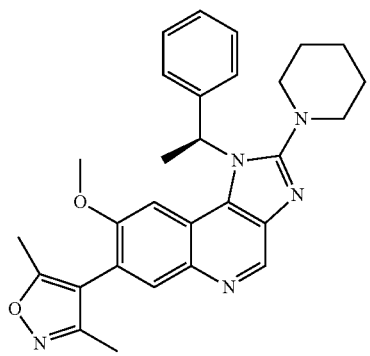 [SMILES: COc1cc2c(cc1-c1c(C)noc1C)ncc1nc(N3CCCCC3)n([C@@H](C)c3ccccc3)c12]

2-Chloro-7-(3,5-dimethyl-4-isoxazolyl)-8-(methyloxy)-1-[(1R)-1-phenylethyl]-1H-imidazo[4,5-c]quinoline (30 mg, 0.069 mmol) (for a preparation see Intermediate 12) was dissolved in NMP (0.5 ml), piperidine (0.2 ml, 2.020 mmol) was added and the mixture was heated at 150° C. for 30 min, then cooled, added to water (10 ml) and extracted with EtOAc (10 ml). The solvent was washed with water (2×10 ml), dried and evaporated. The residue was dissolved in DCM (2 ml), loaded onto a 10 g silica column, eluted with 2M methanolic ammonia/DCM (0-10%) and product-containing fractions evaporated in vacuo to give 7-(3,5-dimethyl-4-isoxazolyl)-8-(methyloxy)-1-[(1R)-1-phenylethyl]-2-(1-piperidinyl)-1H-imidazo[4,5-c]quinoline (18 mg, 0.037 mmol, 53.9% yield) as a amber solid. LCMS (formate) Rt 1.05 min, MH+ 482

Example 18

7-(3,5-dimethyl-4-isoxazolyl)-8-(methyloxy)-2-(4-morpholinyl)-1-(tetrahydro-2H-pyran-4-ylmethyl)-1H-imidazo[4,5-c]quinoline

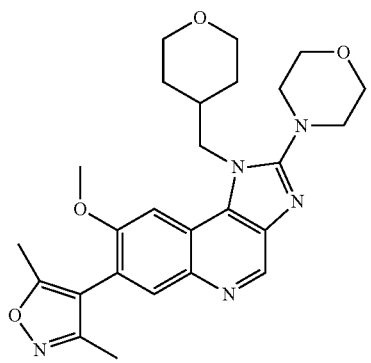 [SMILES: COc1cc2c(cc1-c1c(C)noc1C)ncc1nc(N3CCOCC3)n(CC3CCOCC3)c12]

7-(3,5-Dimethyl-4-isoxazolyl)-8-(methyloxy)-1-(tetrahydro-2H-pyran-4-ylmethyl)-1,3-dihydro-2H-imidazo[4,5-c]quinolin-2-one (220 mg, 0.539 mmol) (for a preparation see intermediate 14) was dissolved in POCl$_3$ (2 ml, 21.46 mmol), PCl$_5$ (0.2 g, 0.960 mmol) was added and the mixture was heated at 120° C. for 24 h. The reaction mixture was evaporated in vacuo to give a beige solid. The solid was dissolved in NMP (0.5 ml) and morpholine (0.3 ml, 3.44 mmol) was added, then the solution was heated in the microwave at 150° C. for 1 h. The solution was loaded onto a 20 g SCX-2 cartridge and washed with methanol (30 ml), then eluted with 2M methanolic ammonia (30 ml) and the eluant evaporated in vacuo to give a beige gum. This was dissolved in DCM (3 ml) and loaded onto a 25 g silica column, then eluted with 2M methanolic ammonia/DCM (0-10%, 25 column volumes) and product containing fractions were evaporated in vacuo to give 7-(3,5-dimethyl-4-isoxazolyl)-8-(methyloxy)-2-(4-morpholinyl)-1-(tetrahydro-2H-pyran-4-ylmethyl)-1H-imidazo[4,5-c]quinoline (4.7 mg, 9.84 μmol, 1.827% yield) as a beige solid. LCMS (formate) Rt 0.70 min, MH+ 478

Example 19

7-(3,5-dimethylisoxazol-4-yl)-N-ethyl-8-methoxy-1-(1-(1-methyl-1H-pyrazol-4-yl)ethyl)-1H-imidazo[4,5-c]quinolin-2-amine

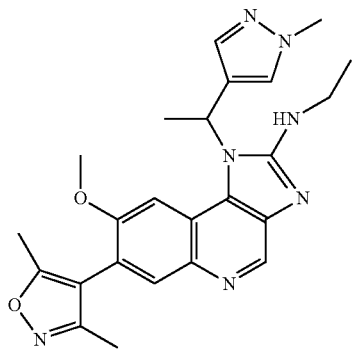 [SMILES: CCNc1nc2cnc3cc(-c4c(C)noc4C)c(OC)cc3c2n1C(C)c1cnn(C)c1]

7-(3,5-Dimethylisoxazol-4-yl)-6-methoxy-N4-(1-(1-methyl-1H-pyrazol-4-yl)ethyl)quinoline-3,4-diamine (70 mg, 0.178 mmol, for a preparation see intermediate 22) was dissolved in ethanol (5 ml) and ethylisothiocyanate (31.1 mg, 0.357 mmol) was added. The solution was heated at 60° C. for 3 h, then cooled and evaporated in vacuo. The residue was dissolved in THF and heated to 60° C. for 4 h, then evaporated in vacuo and the residue dissolved in DMSO and purified by MDAP (formic method. The product-containing fractions were evaporated in vacuo to give 7-(3,5-dimethylisoxazol-4-yl)-N-ethyl-8-methoxy-1-(1-(1-methyl-1H-pyrazol-4-yl)ethyl)-1H-imidazo[4,5-c]quinolin-2-amine (32 mg, 0.072 mmol, 40.3% yield) as a beige solid. LCMS (formate) Rt 0.71 min, MH+ not found.

Example 20

7-(3,5-dimethylisoxazol-4-yl)-8-methoxy-N,N-dimethyl-1-((tetrahydro-2H-pyran-4-yl)methyl)-1H-imidazo[4,5-c]quinolin-2-amine

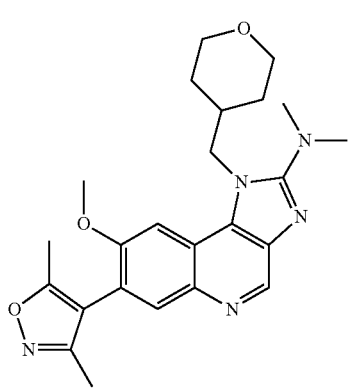 [SMILES: COc1cc2c(cc1-c1c(C)noc1C)ncc1nc(N(C)C)n(CC3CCOCC3)c12]

7-(3,5-Dimethylisoxazol-4-yl)-6-methoxy-N⁴-((tetrahydro-2H-pyran-4-yl)methyl)quinoline-3,4-diamine (for preparation see intermediate 17) (50 mg, 0.131 mmol) and N-(dichloromethylene)-N-methylmethanaminium chloride (available from Aldrich) (42.5 mg, 0.261 mmol) were combined in anhydrous acetonitrile (0.5 ml) and heated at 120° C. for 10 min (microwave). The reaction mixture was reduced to dryness under a stream of nitrogen and the residue dissolved in DMSO (1 ml) and purified by MDAP (HpH). The solvent was evaporated under a stream of nitrogen to give 7-(3,5-dimethylisoxazol-4-yl)-8-methoxy-N,N-dimethyl-1-((tetrahydro-2H-pyran-4-yl)methyl)-1H-imidazo[4,5-c]quinolin-2-amine (44 mg, 0.101 mmol, 77% yield) as a yellow gum.

LCMS (formate) Rt 0.70 mins, MH⁺ 436

Example 21

7-(3,5-dimethylisoxazol-4-yl)-8-methoxy-N-(2-methoxyethyl)-1-((R)-1-(pyridin-2-yl)ethyl)-1H-imidazo[4,5-c]quinolin-2-amine

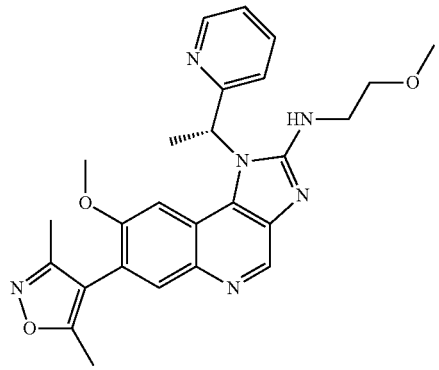 [SMILES: COCCNc1nc2cnc3cc(-c4c(C)noc4C)c(OC)cc3c2n1[C@H](C)c1ccccn1]

To a solution of 7-(3,5-dimethylisoxazol-4-yl)-6-methoxy-N⁴—((R)-1-(pyridin-2-yl)ethyl)quinoline-3,4-diamine (for a preparation, see Intermediate 25) (538 mg, 1.38 mmol) in EtOH (40 mL) was added 1-isothiocyanato-2-methoxyethane (0.30 mL, 2.76 mmol) and the mixture heated at 60° C. for 5.5 h. A further portion of 1-isothiocyanato-2-methoxyethane (0.15 mL, 1.38 mmol) was added and the reaction mixture heated at 60° C. overnight. The mixture was concentrated in vacuo, the residue dissolved in THF (40 mL), EDC (530 mg, 2.76 mmol) added, and the mixture heated at 60° C. for 4 h. The mixture was concentrated in vacuo and the residue purified by chromatography (100 g column, 2M methanolic ammonia/DCM gradient) to give the crude product which was further purified by MDAP (HpH) to give 7-(3,5-dimethylisoxazol-4-yl)-8-methoxy-N-(2-methoxyethyl)-1-((R)-1-(pyridin-2-yl)ethyl)-1H-imidazo[4,5-c]quinolin-2-amine (122 mg, 0.258 mmol, 19% yield) as a white solid. LCMS: (Formate, 2 min), Rt 0.73 mins, MH⁺ 473.

Reference Compounds

Experimental details of LC-MS methods D and F as referred to in the Reference compounds below are as follows:

LC/MS (Method D) was conducted on a Supelcosil LCABZ+PLUS column (3 μm, 3.3 cm×4.6 mm ID) eluting with 0.1% HCO₂H and 0.01 M ammonium acetate in water (solvent A), and 95% acetonitrile and 0.05% HCO₂H in water (solvent B), using the following elution gradient 0-0.7 minutes 0% B, 0.7-4.2 minutes 0→100% B, 4.2-5.3 minutes 100% B, 5.3-5.5 minutes 100→0% B at a flow rate of 3 mL/minute. The mass spectra (MS) were recorded on a Fisons VG Platform mass spectrometer using electrospray positive ionisation [(ES+ve to give [M+H]⁺ and [M+NH₄]⁺ molecular ions] or electrospray negative ionisation [(ES−ve to give [M−H]− molecular ion] modes. Analytical data from this apparatus are given with the following format: [M+H]⁺ or [M−H]⁻.

LC/MS (Method F) was conducted on an Sunfire C18 column (30 mm×4.6 mm i.d. 3.5 μm packing diameter) at 30 degrees centigrade, eluting with 0.1% v/v solution of trifluoroacetic acid in water (Solvent A) and 0.1% v/v solution of trifluoroacetic acid in acetonitrile (Solvent B) using the following elution gradient 0-0.1 min 3% B, 0.1-4.2 min 3-100% B, 4.2-4.8 min 100% B, 4.8-4.9 min 100-3% B, 4.9-5.0 min 3% B at a flow rate of 3 ml/min. The UV detection was an averaged signal from wavelength of 210 nm to 350 nm and mass spectra were recorded on a mass spectrometer using positive electrospray ionization. Ionisation data was rounded to the nearest integer.

LC/HRMS: Analytical HPLC was conducted on a Uptisphere-hsc column (3 μm 33×3 mm id) eluting with 0.01M ammonium acetate in water (solvent A) and 100% acetonitrile (solvent B), using the following elution gradient 0-0.5 minutes 5% B, 0.5-3.75 minutes 5→100% B, 3.75-4.5 100% B, 4.5-5 100→5% B, 5-5.5 5% B at a flow rate of 1.3 mL/minute. The mass spectra (MS) were recorded on a micromass LCT mass spectrometer using electrospray positive ionisation [ES+ve to give MH⁺ molecular ions] or electrospray negative ionisation [ES−ve to give (M−H)− molecular ions] modes.

TLC (thin layer chromatography) refers to the use of TLC plates sold by Merck coated with silica gel 60 F254.

Reference compound A:
2-methyl-6-(methyloxy)-4H-3,1-benzoxazin-4-one

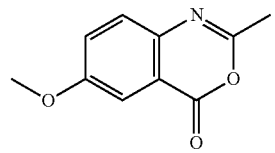

A solution of 5-methoxyanthranilic acid (Lancaster) (41.8 g, 0.25 mol) was refluxed in acetic anhydride (230 ml) for 3.5 h before being concentrated under reduced pressure. The crude compound was then concentrated twice in the presence of toluene before being filtered and washed twice with ether to yield to the title compound (33.7 g, 71% yield) as a brown solid; LC/MS (Method D): m/z 192 [M+H]⁺, Rt 1.69 min.

Reference compound B: [2-amino-5-(methyloxy)phenyl](4-chlorophenyl)methanone

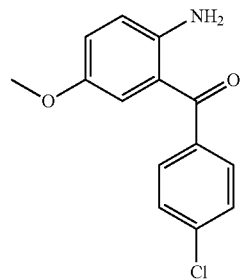 [SMILES: COc1ccc(N)c(C(=O)c2ccc(Cl)cc2)c1]

To a solution of 2-methyl-6-(methyloxy)-4H-3,1-benzoxazin-4-one (for a preparation see Reference compound A) (40.0 g, 0.21 mol) in a toluene/ether (2/1) mixture (760 ml) at 0° C. was added dropwise a solution of 4-chlorophenylmagnesium bromide (170 ml, 1M in diethyl ether, 0.17 mol). The reaction mixture was allowed to warm to room temperature and stirred for 1 h before being quenched with 1N HCl (200 ml). The aqueous layer was extracted with EtOAc (3×150 ml) and the combined organics were washed with brine (100 ml), dried over Na$_2$SO$_4$, filtered and concentrated under reduced pressure. The crude compound was then dissolved in ethanol (400 ml) and 6N HCl (160 ml) was added. The reaction mixture was refluxed for 2 h before being concentrated to one-third in volume. The resulting solid was filtered and washed twice with ether before being suspended in EtOAc and neutralised with 1N sodium hydroxide. The aqueous layer was extracted with EtOAc (3×150 ml) and the combined organics were washed with brine (150 ml), dried over Na$_2$SO$_4$, filtered and concentrated under reduced pressure. The title compound was obtained as a yellow solid (39 g, 88% yield); LC/MS (Method D): m/z 262 [M+H]$^+$, Rt 2.57 min.

Reference Compound C: Methyl N$^1$-[2-[(4-chlorophenyl)carbonyl]-4-(methyloxy)phenyl]-N$^2$-{[(9H-fluoren-9-ylmethyl)oxy]carbonyl}-L-☐-asparaginate

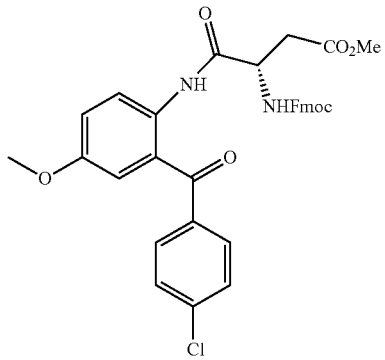

Methyl N-{[(9H-fluoren-9-ylmethyl)oxy]carbonyl}-L-α-aspartyl chloride (*Int. J. Peptide Protein Res.* 1992, 40, 13-18) (93 g, 0.24 mol) was dissolved in CHCl$_3$ (270 ml) and [2-amino-5-(methyloxy)phenyl](4-chlorophenyl)methanone (for a preparation see Reference compound B) (53 g, 0.2 mol) was added. The resulting mixture was stirred at 60° C. for 1 h before being cooled and concentrated at 60% in volume. Ether was added at 0° C. and the resulting precipitate was filtered and discarded. The filtrate was concentrated under reduced pressure and used without further purification.

Reference compound D: Methyl [(3S)-5-(4-chlorophenyl)-7-(methyloxy)-2-oxo-2,3-dihydro-1H-1,4-benzodiazepin-3-yl]acetate

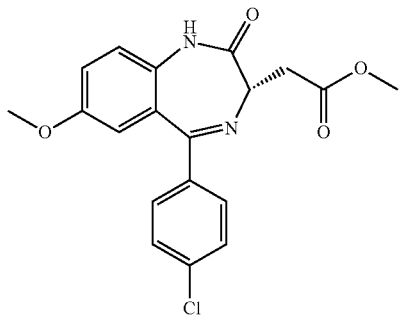

To a solution of methyl N1-[2-[(4-chlorophenyl)carbonyl]-4-(methyloxy)phenyl]-N2-{[(9H-fluoren-9-ylmethyl)oxy]carbonyl}-L-α-asparaginate (for a preparation see Reference compound C) (assumed 0.2 mol) in DCM (500 ml) was added Et$_3$N (500 ml, 3.65 mol) and the resulting mixture was refluxed for 24 h before being concentrated. The resulting crude amine was dissolved in 1,2-DCE (1.5 L) and AcOH (104 ml, 1.8 mol) was added carefully. The reaction mixture was then stirred at 60° C. for 2 h before being concentrated in vacuo and dissolved in DCM. The organic layer was washed with 1N HCl and the aqueous layer was extracted with DCM (×3). The combined organic layers were washed twice with water, and brine, dried over Na$_2$SO$_4$, filtered and concentrated under reduced pressure. The crude solid was recrystallised in MeCN leading to the title compound (51 g) as a pale yellow solid. The filtrate could be concentrated and recrystallised in MeCN to give to another 10 g of the desired product R$_f$=0.34 (DCM/MeOH:95/5).

HRMS MH+calculated for C$_{19}$H$_{18}$$^{35}$ClN$_2$O$_4$ 373.0955. found 373.0957.

Reference compound E: Methyl [(3S)-5-(4-chlorophenyl)-7-(methyloxy)-2-thioxo-2,3-dihydro-1H-1,4-benzodiazepin-3-yl]acetate

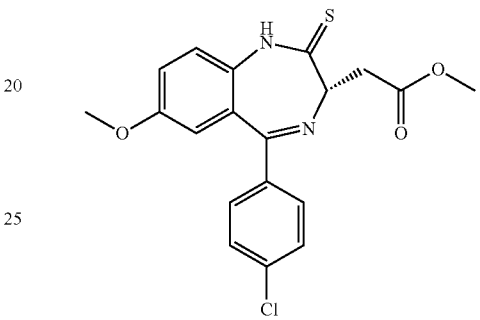

A suspension of P$_4$S$_{10}$ (36.1 g, 81.1 mmol) and Na$_2$CO$_3$ (8.6 g, 81.1 mmol) in 1,2-DCE (700 ml) at room temperature was stirred for 2 h before methyl [(3S)-5-(4-chlorophenyl)-7-(methyloxy)-2-oxo-2,3-dihydro-1H-1,4-benzodiazepin-3-yl]acetate (for a preparation see Reference compound D) (16.8 g, 45.1 mmol) was added. The resulting mixture was stirred at 70° C. for 2 h before being cooled and filtered. The solid was washed twice with DCM and the filtrate washed with sat. Sodium hydrogen carbonate and brine. The organic layer was dried over Na$_2$SO$_4$, filtered and concentrated under reduced pressure. The crude product was purified by flash-chromatography on silica gel (DOM/MeOH: 99/1) to afford the title compound (17.2 g, 98% yield) as a yellowish solid. LC/MS (Method D): m/z 389 [M($^{35}$Cl)+H]$^+$, Rt 2.64 min HRMS MH+calculated for C$_{19}$H$_{18}$$^{35}$ClN$_2$O$_3$S 389.0727. found 389.0714.

Reference compound F: Methyl [(3S)-2-[(1Z)-2-acetylhydrazino]-5-(4-chlorophenyl)-7-(methyloxy)-3H-1,4-benzodiazepin-3-yl]acetate

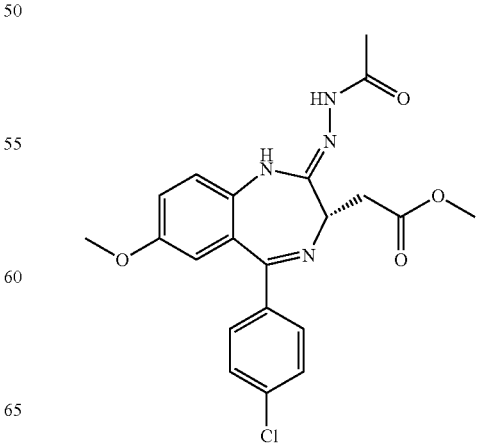

To a suspension of methyl [(3S)-5-(4-chlorophenyl)-7-(methyloxy)-2-thioxo-2,3-dihydro-1H-1,4-benzodiazepin-3-yl]acetate (for a preparation see Reference compound E (9.0 g, 23.2 mmol) in THF (300 ml) at 0° C. was added hydrazine monohydrate (3.4 ml, 69.6 mmol) dropwise. The reaction mixture was stirred for 5 h between 5° C. and 15° C. before being cooled at 0° C. Et₃N (9.7 ml, 69.6 mmol) was then added slowly and acetyl chloride (7.95 ml, 69.6 mmol) was added dropwise. The mixture was then allowed to warm to room temperature for 16 h before being concentrated under reduced pressure. The crude product was dissolved in DCM and washed with water. The organic layer was dried over Na₂SO₄, filtered and concentrated in vacuo to give the crude title compound (9.7 g, 98% yield) which was used without further purification. R$_f$=0.49 (DCM/MeOH:90/10).

Reference compound G: Methyl [(4S)-6-(4-chlorophenyl)-1-methyl-8-(methyloxy)-4H-[1,2,4]triazolo[4,3-a][1,4]benzodiazepin-4-yl]acetate

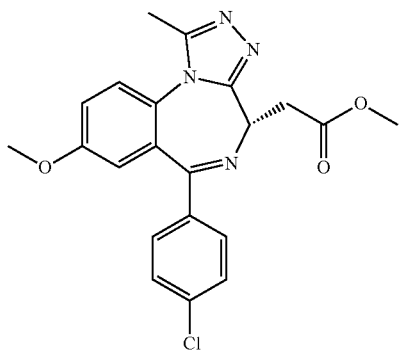

The crude methyl [(3S)-2-[(1Z)-2-acetylhydrazino]-5-(4-chlorophenyl)-7-(methyloxy)-3H-1,4-benzodiazepin-3-yl] acetate (for a preparation see Reference compound F) (assumed 9.7 g) was suspended in THF (100 ml) and AcOH (60 ml) was added at room temperature. The reaction mixture was stirred at this temperature for 2 days before being concentrated under reduced pressure. The crude solid was triturated in i-Pr₂O and filtered to give the title compound (8.7 g, 91% over 3 steps) as an off-white solid.

HRMS MH+calculated for C₂₁H₂₀ClN₄O₃ 411.1229. found 411.1245.

Reference compound H: [(4S)-6-(4-Chlorophenyl)-1-methyl-8-(methyloxy)-4H-[1,2,4]triazolo[4,3-a][1,4]benzodiazepin-4-yl]acetic acid

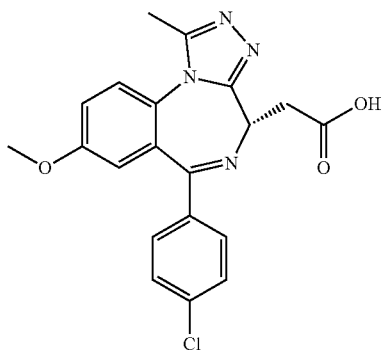 [SMILES: COc1ccc2c(c1)C(c1ccc(Cl)cc1)=N[C@@H](CC(=O)O)c1nnc(C)n1-2]

To a solution of methyl [(4S)-6-(4-chlorophenyl)-1-methyl-8-(methyloxy)-4H-[1,2,4]triazolo[4,3-a][1,4]benzodiazepin-4-yl]acetate (for a preparation see Reference compound G) (7.4 g, 18.1 mmol) in THF (130 ml) at room temperature was added 1N sodium hydroxide (36.2 ml, 36.2 mmol). The reaction mixture was stirred at this temperature for 5 h before being quenched with 1N HCl (36.2 ml) and concentrated in vacuo. Water is then added and the aqueous layer was extracted with DCM (×3) and the combined organic layers were dried over Na₂SO₄, filtered and concentrated under reduced pressure to give the title compound (7 g, 98% yield) as a pale yellow solid.

Reference compound H: 1,1-dimethylethyl[5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate

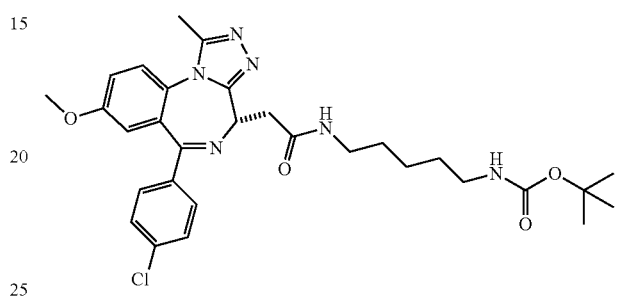

A mixture of [(4S)-6-(4-chlorophenyl)-1-methyl-8-(methyloxy)-4H-[1,2,4]triazolo[4,3-a][1,4]benzodiazepin-4-yl] acetic acid (for a preparation see Reference compound G) (1.0 g, 2.5 mmol), HATU (1.9 g, 5 mmol) and DIPEA (0.88 ml, 5 mmol) was stirred for 80 minutes at room temperature, to this was added 1,1-dimethylethyl (4-aminobutyl)carbamate (1.05 ml, 5.0 mmol, available from Aldrich). The reaction mixture was stirred at room temperature for 2 h before it was concentrated. The residue was taken up in dichloromethane and washed with 1N HCl. The aqueous layer was extracted with dichloromethane twice. Organic layer was washed with 1N sodium hydroxide, followed by a saturated solution of sodium chloride, dried over sodium sulphate and concentrated. The residue was purified by flash-chromatography on silica using dichloromethane/methanol 95/5 to give the title compound as a yellow solid (1.2 g). LC/MS (Method D): rt=3.04 min.

Reference compound J: N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate

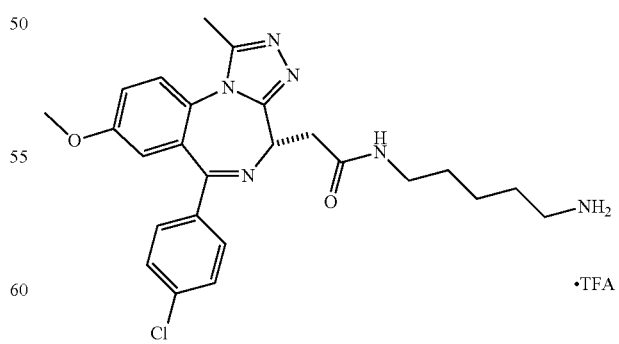

To a solution of 1,1-dimethylethyl[5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate (for a preparation see Reference compound H) (0.2 g, 0.34 mmol) in dichloromethane (3 ml) was added trifluoroacetic acid (0.053 ml, 0.68 mmol) dropwise at 0° C. The reaction mixture was stirred for 3 h from 0° C. to room temperature. The reaction mixture was concentrated to dryness to afford the title compound as a hygroscopic yellow oil (200 mg)

LC/MS (Method D): rt=2.33 min.

HRMS MH+calculated for $C_{25}H_{29}ClN_6O_2$ 481.2119. found 481.2162.

Reference compound K: Mixture of 5- and 6-isomers of Alexa Fluor 488-N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide mixture vortex mixed overnight. After 18 h the reaction mixture was evaporated to dryness and the residue redissolved in DMSO/water (50%, <1 ml total), applied to a preparative Phenomenex Jupiter C18 column and eluted with a gradient of 95% A: 5% B to 100% B (A=0.1% trifluoroacetic acid in water, B=0.1% TFA/90% acetonitrile/10% water) at a flow rate of 10 ml/min over 150 minutes. Impure fractions were combined and re-purified using the same system. Fractions were combined and evaporated to yield the title product (2.8 mg) as a mixture of the 2 regioisomers shown. LC/MS (Method F): MH+=999, rt=1.88 min.

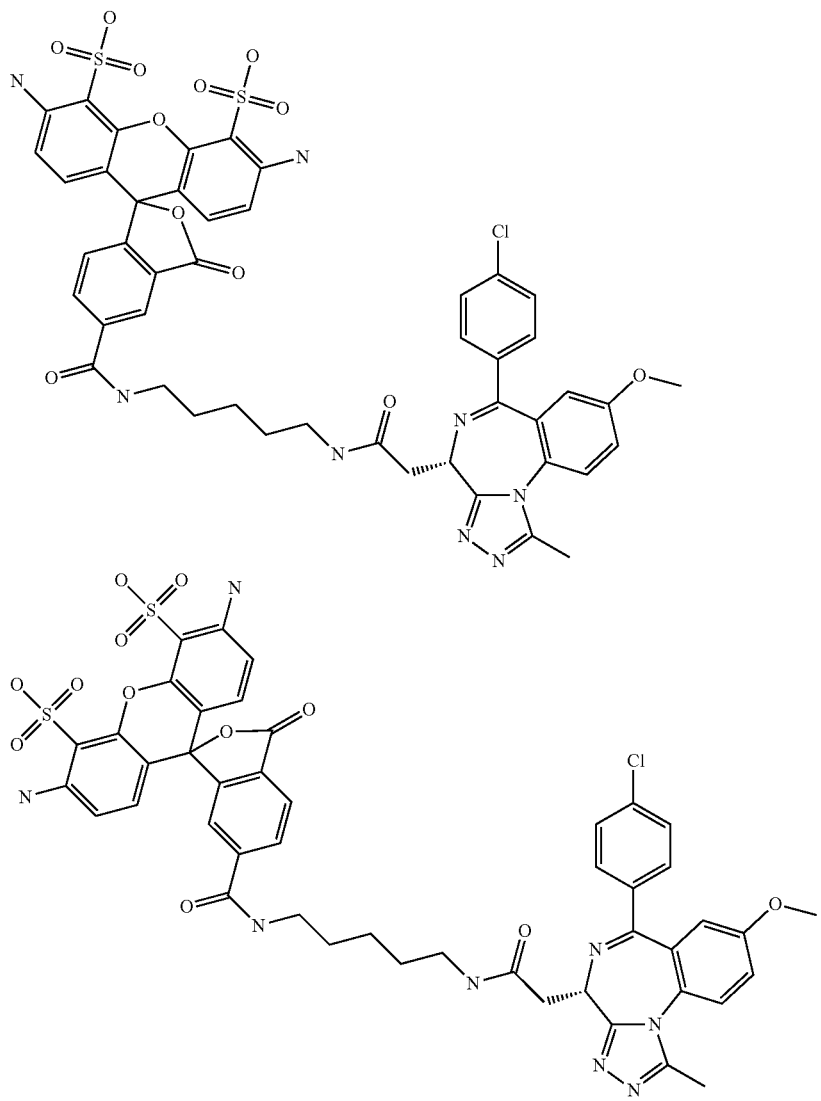

N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate (for a preparation see Reference compound J) (7.65 mg, 0.013 mmol) was dissolved in N,N-dimethylformamide (DMF) (300 μl) and added to Alexa Fluor 488 carboxylic acid succinimidyl ester (5 mg, 7.77 μmol, mixture of 5 and 6 isomers, available from Invitrogen, product number A-20100) in an Eppendorf centrifuge tube. Hunig's base (7.0 μl, 0.040 mmol) was added and the Biological Test Methods Fluorescence Anisotropy Binding Assay The binding of the compounds of formula (I) to Bromodomain BRD2, BRD3 and BRD4 may be assessed using a Fluorescence Anisotropy Binding Assay.

The Bromodomain protein, fluorescent ligand (Reference compound K see above) and a variable concentration of test compound are incubated together to reach thermodynamic equilibrium under conditions such that in the absence of test compound the fluorescent ligand is significantly (>50%) bound and in the presence of a sufficient concentration of a potent inhibitor the anisotropy of the unbound fluorescent ligand is measurably different from the bound value.

All data was normalized to the mean of 16 high and 16 low control wells on each plate. A four parameter curve fit of the following form was then applied:

$$y=a+((b-a)/(1+(10\char`\^x/10\char`\^c)\char`\^d)$$

Where 'a' is the minimum, 'b' is the Hill slope, 'c' is the $pIC_{50}$ and 'd' is the maximum. Recombinant Human Bromodomains (Bromodomain BRD2 (1-473), Bromodomain BRD3 (1-435) and Bromodomain BRD4 (1-477)) were expressed in E. coli cells (in pET15b vector) with a six-His tag at the N-terminal. The His-tagged Bromodomain was extracted from E. coli cells using 0.1 mg/ml lysozyme and sonication. The Bromodomain was then purified by affinity chromatography on a HisTRAP HP column, eluting with a linear 10-500 mM Imidazole gradient, over 20 Cv. Further purification was completed by Superdex 200 prep grade size exclusion column. Purified protein was stored at –80° C. in 20 mM HEPES pH 7.5 and 100 mM NaCl.

Protocol for Bromodomain BRD2: All components were dissolved in buffer composition of 50 mM HEPES pH7.4, 150 mm NaCl and 0.5 mM CHAPS with final concentrations of Bromodomain 2, 75 nM, fluorescent ligand 5 nM. 10 µl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision (λex=485 nm, λEM=530 nm; Dichroic—505 nM).

Protocol for Bromodomain BRD3: All components were dissolved in buffer of composition 50 mM HEPES pH7.4, 150 mm NaCl and 0.5 mM CHAPS with final concentrations of Bromodomains 3 75 nM, fluorescent ligand 5 nM. 10 µl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision (λex=485 nm, λEM=530 nm; Dichroic—505 nM).

Protocol for Bromodomain BRD4: All components were dissolved in buffer of composition 50 mM HEPES pH7.4, 150 mm NaCl and 0.5 mM CHAPS with final concentrations of Bromodomain 4 75 nM, fluorescent ligand 5 nM. 10 µl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision (λex=485 nm, λEM=530 nm; Dichroic—505 nM).

Time Resolved Fluorescence Resonance Energy Transfer (TR-FRET) Assay

The binding of the compounds of formula (I) to Bromodomains BRD2, BRD3 and BRD4 was assessed using a time resolved fluorescent resonance energy transfer binding assay, that measures the binding of an acetylated histone peptide to the bromodomain protein.

The bromodomain protein, histone peptide and a variable concentration of test compound are incubated together to reach thermodynamic equilibrium. The assay is configured such that in the absence of test compound the bromodomain and peptide are significantly bound (~30%) and in the presence of a sufficient concentration of a potent inhibitor this interaction is disrupted leading to a measurable drop in fluorescent resonance energy transfer.

Histone Peptide:

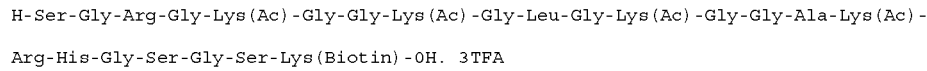

The protected peptide was assembled on a solid-phase synthesiser using preloaded Wang resin and utilising standard Fmoc synthesis protocols. The C-terminal lysine was protected by a hyper acid-labile group allowing for its selective removal at the end of the assembly and attachment of the biotin. The crude peptide was obtained after cleavage from the resin with a mixture of trifluoroacetic acid (TFA), triisopropylsilane and water (95:2.5:2.5) for 3 h at room temperature and was then purified using a C18 reverse-phase column utilising a 0.1% TFA-buffered water/acetonitrile gradient. The resulting fractions were analysed and fractions which were >95% pure by analytical HPLC and giving the correct mw (by MALDiTOF mass spectroscopy) were pooled and freeze dried. The final material was analysed by HPLC to confirm purity.

Protein Production: Recombinant Human Bromodomains (BRD2 (1-473), BRD3 (1-435) and BRD4 (1-477)) were expressed in E. coli cells (in pET15b vector) with a six-His tag at the N-terminal. The His-tagged Bromodomain was extracted from E. coli cells using sonication and purified using a nickel sepharose 6FF column, the proteins were washed and then eluted with 50 mM Tris-Hcl pH8.0. 300 mM NaCl, 1 mM 3-mercaptoethanol and 20 mM Imidazole. Further purification was performed by affinity chromatography on a HisTRAP HP column, eluting with a linear 0-500 mM sodium chloride gradient, over 20 column volumes. Final purification was completed by Superdex 200 prep grade size exclusion column. Purified protein was stored at –80 C in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3 and 4 Assays: All assay components were dissolved in buffer composition of 50 mM HEPES pH7.4, 50 mM NaCl and 0.5 mM CHAPS. The final concentration of bromodomain proteins were 100 nM and the histone peptide was 300 nM, these components are premixed and allowed to equilibrate for 1 hour in the dark. 8 µl of this reaction mixture was added to all wells containing 50 nl of various concentrations of test compound or DMSO vehicle (0.5% final) in Greiner 384 well black low volume microtitre plates and incubated in dark for 60 mins at room temperature. 2 µl of detection mixture containing anti-6his XL665 labeled antibody and streptavidin labeled with europium cryptate was added to all wells and a further dark incubation of at least 30 mins was performed. Plates were then read on the Envision platereader, (λex=317 nm, donor λEM=615 nm; acceptor λEM=665 nm; Dichroic LANCE dual). Time resolved fluorescent intensity measurements were made at both emission wavelengths and the ratio of acceptor/donor was calculated and used for data analysis. All data was normalized to the mean of 16 high and 16 low control wells on each plate. A four parameter curve fit of the following form was then applied:

$$y=a+((b-a)/(1+(10^x/10^c)^d)$$

Where 'a' is the minimum, 'b' is the Hill slope, 'c' is the pIC50 and 'd' is the maximum.

Examples 1-21 were tested in each of the above assays and were found to have a pIC50 in the range 6.0 to 7.3. Examples 1, 4, 6-10, 13, 15-18, 20 and 21 were found to have a pIC50 in the range 7.0 to 7.3 in at least one of the above assays.

Measurement of LPS Induced IL-6 Secretion from Whole Blood

Activation of monocytic cells by agonists of toll-like receptors such as bacterial lipopolysaccharide (LPS) results in production of key inflammatory mediators including IL-6. Such pathways are widely considered to be central to the pathophysiology of a range of auto-immune and inflammatory disorders.

Compounds to be tested are diluted to give a range of appropriate concentrations of which 1 μl of the diluted stocks is added to a 96 well plate. Following addition of whole blood (130 μl) the plates are incubated at 37 degrees (5% CO2) for 30 min before the addition of 10 μl of 2.8 ug/ml LPS, diluted in complete RPMI 1640 (final concentration=200 ng/ml), to give a total volume of 140 ul per well. After further incubation for 24 hours at 37 degrees, 140 μl of PBS are added to each well. The plates are sealed, shaken for 10 minutes and then centrifuged (2500 rpm×10 min). 100 μl of the supernatant are removed and IL-6 levels assayed by immunoassay (typically by MesoScale Discovery technology) either immediately or following storage at −20 degrees. Concentration response curves for each compound was generated from the data and an IC$_{50}$ value was calculated Examples 1-3, 6-11, 14, 18, 20 and 21 were tested in the above assay were found to have a pIC50 in the range 5 5-7.0 apart from Examples 2 and 8 which had a pIC50<5.5.

These data demonstrate that bromodomain inhibitors tested in the above whole blood assay inhibited the production of key inflammatory mediator IL-6.

In Vivo Mouse Endotoxemia Model

High doses of Endotoxin (bacterial lipopolysaccharide) administered to animals produce a profound shock syndrome including a strong inflammatory response, dysregulation of cardiovascular function, organ failure and ultimately mortality. This pattern of response is very similar to human sepsis and septic shock, where the body's response to a significant bacterial infection can be similarly life threatening.

To test the compounds for use in the invention groups of eight Balb/c male mice are given a lethal dose of 15 mg/kg LPS by intraperitoneal injection. Ninety minutes later, animals were dosed intravenously with vehicle (20% cyclodextrin 1% ethanol in apyrogen water) or compound (10 mg/kg). The survival of animals is monitored at 4 days.

Oncology Cell Growth Assay

Human cell lines (n=33 comprising 15 heme cell lines, 14 breast cell lines and 4 other cell lines) were cultured in RPMI-1640 containing 10% fetal bovine serum, 1000 viable cells per well were plated in 384-well black flat bottom polystyrene plates (Greiner #781086) in 48 μl of culture media. All plates were placed at 5% CO$_2$, 37° C. overnight. The following day one plate was harvested with CellTiter-Glo (CTG, Promega #G7573) for a time equal to 0 (T0) measurement and compound (20 point titration from 14.7 uM to 7 pM) was added to the remaining plates. The final concentration of DMSO in all wells was 0.15%. Cells were incubated for 72 hours or the indicated time and each plate was developed with CellTiter-Glo reagent using a volume equivalent to the cell culture volume in the wells. Plates were shaken for approximately 2 minutes and chemiluminescent signal was read on the Analyst GT (Molecular Devices) or EnVision Plate Reader (Perkin Elmer).

Results are expressed as a percent of the T0 and plotted against the compound concentration. The T0 value was normalized to 100% and represents the number of cells at time of compound addition and the concentration response data were fit with a 4 parameter curve fit using XLfit software (model 205). The concentration that inhibited cell growth by 50% (gIC$_{50}$) is the midpoint of the 'growth window' (between the T0 and DMSO control). The Ymin−T0 value is determined by subtracting the T0 value (100%) from the Ymin value (%) determined from the fit of the concentration response curve. Values from the wells with no cells were subtracted from all samples for background correction.

All publications, including but not limited to patents and patent applications, cited in this specification are herein incorporated by reference as if each individual publication were specifically and individually indicated to be incorporated by reference herein as though fully set forth.

The invention claimed is:

1. A compound of formula (I) or a salt thereof

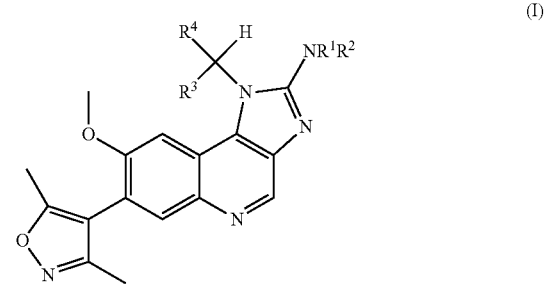

wherein:
R$^1$ is hydrogen or C$_{1-3}$alkyl and R$^2$ is selected from
  hydrogen;
  C$_{1-6}$alkyl; and
  C$_{2-6}$alkyl substituted by hydroxy, C$_{1-4}$alkoxy or a group NR$^a$R$^b$ in which R$^a$ and R$^b$ are independently hydrogen or C$_{1-4}$alkyl, or R$^a$ and R$^b$ combine together with the N to which they are attached to form a heterocyclyl ring; or
R$^1$ and R$^2$ combine together with the N to which they are attached to form a heterocyclyl ring;
R$^3$ is hydrogen, C$_{1-3}$alkyl or CH$_2$OH;
R$^4$ is selected from
  a phenyl group optionally substituted by C$_{1-4}$alkyl, CF$_3$, halogen, hydroxy or C$_{1-4}$alkoxy;
  a heteroaromatic group optionally substituted by C$_{1-4}$alkyl, CF$_3$, halogen, hydroxy or C$_{1-4}$alkoxy;
  a tetrahydropyranyl group;
  a tetrahydrofuranyl group;
  a C$_{3-7}$cycloalkyl group; and
  —CH$_2$OMe.

2. A compound or a salt thereof according to claim 1 in which R$^1$ and R$^2$ combine together with the N to which they are attached to form a piperidinyl or morpholinyl ring.

3. A compound or a salt thereof according to claim 1 in which R$^1$ is hydrogen and R$^2$ is hydrogen or C$_{1-4}$alkyl.

4. A compound or a salt thereof according to claim 1 in which $R^1$ is hydrogen and $R^2$ is $C_{2-4}$alkyl substituted by hydroxy or methoxy.

5. A compound or a salt thereof according to claim 4 in which is the $C_{1-4}$alkyl group group is ethyl.

6. A compound or a salt thereof according to claim 1 in which $R^1$ is hydrogen and $R^2$ is $C_{2-4}$alkyl substituted by $NR^aR^b$ wherein $R^a$ and $R^b$ are both hydrogen or $R^a$ and $R^b$ combine together with the N to which they are attached to form a morpholinyl ring.

7. A compound or a salt thereof according to claim 6 in which the $C_{2-4}$alkyl group is ethyl.

8. A compound or a salt thereof according to claim 1 in which $R^3$ is hydrogen and $R^4$ is tetrahydropyranyl.

9. A compound or a salt thereof according to claim 1 in which $R^3$ is hydrogen or methyl and $R^4$ is pyridyl.

10. A compound or a salt thereof according to claim 1 in which $R^3$ is hydrogen or methyl and $R^4$ is phenyl.

11. A compound or a salt thereof according to claim 1 in which $R^3$ is methyl and $R^4$ is a group —$CH_2OMe$.

12. A compound which is selected from
2-({7-(3,5-dimethyl-4-isoxazolyl)-8-(methyloxy)-1-[(1R)-1-phenylethyl]-1 H-imidazo[4,5-c]quinolin-2-yl}amino)ethanol;
2-{[7-(3,5-dimethyl-4-isoxazolyl)-8-(methyloxy)-1-(tetrahydro-2H-pyran-4-ylmethyl)-1H-imidazo[4,5-c]quinolin-2-yl]amino}ethanol;
7-(3,5-dimethyl-4-isoxazolyl)-8-(methyloxy)-1-(tetrahydro-2H-pyran-4-ylmethyl)-1 H-imidazo[4,5-c]quinolin-2-amine;
7-(3,5-dimethyl-4-isoxazolyl)-8-(methyloxy)-1-(2-pyridinylmethyl)-1H-imidazo[4,5-c]quinolin-2-amine;
7-(3,5-dimethyl-4-isoxazolyl)-1-[methyl-2-(methyloxy)ethyl]-8-(methyloxy)-1 H-imidazo[4,5-c]quinolin-2-amine;
7-(3,5-dimethyl-4-isoxazolyl)-N-ethyl-8-(methyloxy)-1-(tetrahydro-2H-pyran-4-ylmethyl)-1H-imidazo[4,5-c]quinolin-2-amine;
7-(3,5-dimethylisoxazol-4-yl)-N-ethyl-8-methoxy-1-(1-methoxypropan-2-yl)-1H-imidazo[4,5-c]quinolin-2-amine;
N1-(7-(3,5-dimethylisoxazol-4-yl)-8-methoxy-1-((tetrahydro-2H-pyran-4-yl)methyl)-1H-imidazo[4,5-c]quinolin-2-yl)ethane-1,2-diamine;
7-(3,5-dimethyl-4-isoxazolyl)-8-(methyloxy)-N-[2-(4-morpholinyl)ethyl]-1-(tetrahydro-2H-pyran-4-ylmethyl)-1H-imidazo[4,5-c]quinolin-2-amine;
7-(3,5-dimethyl-4-isoxazolyl)-8-(methyloxy)-N-[2-(methyloxy)ethyl[-1-(tetrahydro-2H-pyran-4-ylmethyl)-1H-imidazo[4,5-c]quinolin-2-amine;
7-(3,5-dimethyl-4-isoxazolyl)-N-ethyl-1-[1-methyl-2-(methyloxy)ethyl]-8-(methyloxy)-1H-imidazo[4,5-c]quinolin-2-amine;
N-[7-(3,5-dimethyl-4-isoxazolyl)-1[1-methyl-2-(methyloxy)ethyl]-8-(methyloxy)-1H-imidazo[4,5-c]quinolin-2-yl]-1,2-ethanediamine;
7-(3,5-dimethyl-4-isoxazolyl)-1[1-methyl-2-(methyloxy)ethyl]-8-(methyloxy)-N-[2-(4-morpholinyl)ethyl]-1H-imidazo[4,5-c]quinolin-2-amine;
7-(3,5-dimethyl-4-isoxazolyl)-1[1-methyl-2-(methyloxy)ethyl]-8-(methyloxy)-N-[2-(methyloxy)ethyl]-1H-imidazo[4,5-c]quinolin-2-amine;
7-(3,5-dimethyl-4-isoxazolyl)-8-(methyloxy)-N-[2-(methyloxy)ethyl]-1-(2-pyridinylmethyl)-1H-imidazo[4,5-c]quinolin-2-amine;
7-(3,5-dimethyl-4-isoxazolyl)-8-(methyloxy)-2-(4-morpholinyl)-1-[(1R)-1-phenylethyl]-1H-imidazo[4,5-c]quinoline;
7-(3,5-dimethyl-4-isoxazolyl)-8-(methyloxy)-1-[(1R)-1-phenylethyl]-2-(1-piperidinyl)-1H-imidazo[4,5-c]quinoline;
7-(3,5-dimethyl-4-isoxazolyl)-8-(methyloxy)-2-(4-morpholinyl)-1-(tetrahydro-2H-pyran-4-ylmethyl)-1H-imidazo[4,5-c]quinoline;
7-(3,5-dimethylisoxazol-4-yl)-N-ethyl-8-methoxy-1-(1-(1-methyl-1H-pyrazol-4-yl)ethyl)-1H-imidazo[4,5-c]quinolin-2-amine;
7-(3,5-dimethylisoxazol-4-yl)-8-methoxy-N,N-dimethyl-1-((tetrahydro-2H-pyran-4-yl)methyl)-1H-imidazo[4,5-c]quinolin-2-amine; and
7-(3,5-dimethylisoxazol-4-yl)-8-methoxy-N-(2-methoxyethyl)-1-((R)-1-(pyridin-2-yl)ethyl)-1H-imidazo[4,5-c]quinolin-2-amine or a salt thereof.

13. A pharmaceutical composition which comprises a compound or a pharmaceutically acceptable salt thereof as defined in claim 1 and one or more pharmaceutically acceptable carriers, diluents or excipients.

* * * * *